United States Patent
Fleming

(10) Patent No.: US 12,062,445 B2
(45) Date of Patent: Aug. 13, 2024

(54) PREDICTING A PATHOLOGICAL CONDITION FROM A MEDICAL IMAGE

(71) Applicant: OPTOS PLC, Dunfermline (GB)

(72) Inventor: Alan Duncan Fleming, Dunfermline (GB)

(73) Assignee: OPTOS PLC, Dunfermline (GB)

( * ) Notice: Subject to any disclaimer, the term of this patent is extended or adjusted under 35 U.S.C. 154(b) by 554 days.

(21) Appl. No.: 16/837,524

(22) Filed: Apr. 1, 2020

(65) Prior Publication Data

US 2020/0320692 A1    Oct. 8, 2020

(30) Foreign Application Priority Data

Apr. 4, 2019 (EP) .................................... 19167392

(51) Int. Cl.
*G16H 50/20* (2018.01)
*A61B 5/00* (2006.01)
*G06T 7/00* (2017.01)

(52) U.S. Cl.
CPC ........... *G16H 50/20* (2018.01); *A61B 5/7275* (2013.01); *G06T 7/0012* (2013.01);
(Continued)

(58) Field of Classification Search
CPC ........ G16H 50/20; G16H 30/40; G16H 50/30; G16H 70/60; G06T 7/0012;
(Continued)

(56) References Cited

U.S. PATENT DOCUMENTS

| 6,091,841 A * | 7/2000 | Rogers .................... G06F 18/41 382/256 |
| 2016/0110584 A1* | 4/2016 | Remiszewski ......... G06V 20/69 382/133 |

(Continued)

FOREIGN PATENT DOCUMENTS

| GB | 2 457 022 A | 8/2009 |
| JP | 2001525579 A | 12/2001 |

(Continued)

OTHER PUBLICATIONS

Kockara, Sinan, et al. "Analysis of density based and fuzzy c-means clustering methods on lesion border extraction in dermoscopy images." BMC bioinformatics. vol. 11. No. 6. BioMed Central, 2010 (Year: 2010).*

(Continued)

*Primary Examiner* — Aaron W Carter
*Assistant Examiner* — Courtney Joan Nelson
(74) *Attorney, Agent, or Firm* — FAEGRE DRINKER BIDDLE & REATH

(57) ABSTRACT

A computer-implemented method, system, and computer-readable medium, for determining a pathologic condition from a medical image of a portion of a subject. The method includes acquiring a plurality of lesion locations in the medical image; applying a clustering algorithm to the plurality of lesion locations to identify at least one lesion cluster and corresponding lesion cluster data; categorizing each lesion cluster into one of a set of predetermined categories based on the identified lesion cluster data; applying at least one function to the lesion cluster data with regard to each category of the set of predetermined categories, wherein the at least one function provides a fixed number of data outputs; and determining a pathologic condition by processing the fixed number of data outputs of each category of the set based on a classification algorithm trained on image data (Continued)

defining medical images of the portion of a plurality of subjects.

20 Claims, 10 Drawing Sheets

(52) U.S. Cl.
CPC .............. *G06T 2207/10081* (2013.01); *G06T 2207/10088* (2013.01); *G06T 2207/20081* (2013.01); *G06T 2207/20084* (2013.01); *G06T 2207/20182* (2013.01); *G06T 2207/30016* (2013.01); *G06T 2207/30061* (2013.01); *G06T 2207/30096* (2013.01)

(58) Field of Classification Search
CPC ... G06T 2207/30096; G06T 7/10; G06T 7/00; G06T 2207/20021; G06T 2207/30004; G06T 2207/10081; G06T 2207/10088; G06T 2207/20081; G06T 2207/20084; G06T 2207/20182; G06T 2207/30016; G06T 2207/30061; A61B 5/7275; A61B 5/7264; A61B 5/444; A61B 5/445; A61B 6/5217; A61B 6/5211
See application file for complete search history.

(56) References Cited

U.S. PATENT DOCUMENTS

| | | |
|---|---|---|
| 2016/0331224 A1 | 11/2016 | Uji et al. |
| 2017/0039412 A1* | 2/2017 | Solanki .................. G06V 10/44 |

FOREIGN PATENT DOCUMENTS

| | | | | |
|---|---|---|---|---|
| JP | 2016214312 A | 12/2016 | | |
| WO | WO 2010/131944 A2 | 11/2010 | | |
| WO | 2017058848 A1 | 4/2017 | | |
| WO | WO-2017058848 A1 * | 4/2017 | ........... | A61B 5/7264 |
| WO | 2018018160 A1 | 2/2018 | | |

OTHER PUBLICATIONS

Rocha, Anderson, et al. "Points of interest and visual dictionaries for automatic retinal lesion detection." IEEE transactions on biomedical engineering 59.8 (2012): 2244-2253 (Year: 2012).*
American Academy of Ophthalmology Retina/Vitreous Panel, Preferred Practice Pattern Guidelines, Age-Related Macular Degeneration, San Francisco, CA: American Academy of Ophthalmology; 2015, (57 sheets), available at www.aao.org/ppp.
American Academy of Ophthalmology Retina/Vitreous Panel, Preferred Practice Pattern Guidelines, Diabetic Retinopathy, San Francisco, CA: American Academy of Ophthalmology; 2017, (63 sheets), available at www.aao.org/ppp.
Notice of Reasons for Rejection issued Jun. 15, 2021 in Japanese patent application No. 2020-068565 (3 sheets) (English translation attached; 4 sheets).
Paolo Sandico Silva et al., Automated Hemorrhage and Microaneurysm Counts on Ultrawide Field Images Predict Increased Risk of Diabetic Retinopathy Progression Over 4 Years, Investigative Ophthalmology & Visual Science, Jul. 2018, vol. 59, 737, Abstract.
Malavika Bhaskaranand, et al., Automated Diabetic Retinopathy Screening and Monitoring Using Retinal Fundus Image Analysis, Journal of Diabetes Science and Technology, vol. 10(2), pp. 254-261 (2016).
Diabetic Retinopathy Guidelines, Scientific Department, the Royal College of Ophthalmologists, pp. 1-147, 2012. (DR Guidelines Expert Working Party Members).
Ayman El-Baz et al., Automatic Detection of 2d and 3d Lung Nodules in Chest Spiral CT Scans, Hindawi Publishing Corporation, International Journal of Biomedical Imaging, vol. 2013, Article ID 517632, pp. 1-11, 2013.
Alan D Fleming, et al., Automated Microaneurysm Detection Using Local Contrast Normalization and Local Vessel Detection. IEEE Transactions on Medical Imaging, vol. 25, No. 9, Sep. 2006, pp. 1223-1232.
Mohamad Habes, et al., White matter lesions: Spatial heterogeneity, links to risk factors, cognition, genetics, and atrophy, Neurology, vol. 91, No. 10, pp. e965-e975 (Sep. 4, 2018).
Konstantin Korotkov, et al., A New Total Body Scanning System for Automatic Change Detection in Multiple Pigmented Skin Lesions, IEEE Transactions on Medical Imaging, vol. 34 No. 1, pp. 317-338 (Jan. 2015).
Geert Litjens, et al., A Survey on Deep Learning in Medical Image Analysis, Medical Image Analysis, 42:60-88 (2017) (sheets 1-38).
Annette McWilliams, et al., Probability of Cancer in Pulmonary Nodules Detected on First Screening CT, the New England Journal of Medicine, 369(10), pp. 910-919 (2013).
Eloy Roura, et al., Automated Detection of Lupus White Matter Lesions in MRI; Frontiers in Neuroinformatics, vol. 10, Article 33, pp. 1-11 (2016).
Paolo S Silva, et al., Hemorrhage and/or Microaneurysm Severity and Count in Ultrawide Field Images and Early Treatment Diabetic Retinopathy Study Photography, American Academy of Ophthalmology, 124(7), pp. 970-976 (2017).
Deborah Sturm, et al., Computer-aided tracking of MS, Proc. of SPIE, vol. 7963, 79632V-1, 7 sheets (2011).
Atsushi Teramoto, et al., Automated detection of pulmonary nodules in PET/CT images: Ensemble false-positive reduction using a convolutional neural network technique, Medical Physics, vol. 43, No. 6, pp. 2821-2827 (Jun. 2016).
Liqun Wang, et al., Survey of the distribution of lesion size in multiple sclerosis: implication for the measurement of total lesion load, Journal of Neurology, Neurosurgery, and Psychiatry, vol. 63(4), pp. 452-455 (1997).
Communication and European Search Report dated May 31, 2019 relating to European patent application No. 19 167 392.0 (15 sheets).
Rocha A. et al., Points of Interest and Visual Dictionaries for Automatic Retinal Lesion Detection, IEEE Transactions on Biomedical Engineering, vol. 59, No. 8, pp. 2244-2253 (Aug. 1, 2012), XP011490160.
Madhukumar S. et al., Visual Dictionary: a Decision Support Tool for Dr Pathology Detection on POI, IEEE Conference on Information Communication and Embedded Systems (ICICES), pp. 496-501 (2013) XP032384015.
Scottish Diabetic Retinopathy Grading Scheme 2007 v1.1, pp. 1-4 (2007).
Lancaster et al., Automated Talairach Atlas Labels for Functional Brain Mapping, Human Brain Mapping, 10(3), pp. 120-131 (2000).
Tzourio-Mazoyer et al., Technical Note, Automated Anatomical Labeling of Activations in SPM Using a Macroscopic Anatomical Parcellation of the MNI MRI Single-Subject Brain, NeuroImage, 15(1), pp. 273-289 (2002).
Jirapatnakul at al., Segmentation of Juxtapleural Pulmonary Nodules Using a Robust Surface Estimate, Hindawi Publishing Corporation, International Journal of Biomedical Imaging, vol. 2011, Article ID 632195, pp. 1-14 (2011).
Office Action issued Feb. 8, 2022 in Japanese application No. 2020-068565 (two sheets); English translation thereof entitled "Decision of Refusal" attached (3 sheets).

\* cited by examiner

PREDICTING A PATHOLOGICAL CONDITION FROM A MEDICAL IMAGE

This application claims the benefit of priority of European Patent Application No. 19 167 392.0, filed Apr. 4, 2019, the entire contents of which are incorporated by reference as if set forth fully herein.

FIELD

Example aspects herein generally relate to the field of image processing and, more particularly, to the processing of a medical image to facilitate the determination of a pathological level or condition indicated in the medical image.

BACKGROUND

Automated image processing technologies have been developed to detect diseases or signatures thereof on the basis of medical digital imaging.

A disease may present as small focal lesions that can be observed in digital images. Lesions, i.e. any damage or abnormal change in tissue, may be caused by diseases or trauma. For example, two retinal diseases which are major worldwide causes of blindness, diabetic retinopathy (DR) and age related macular degeneration (AMD), present, at least in their early stages, with small focal lesions having typical variable sizes of 20 to 150 micrometres. These lesions may occur individually, in small clusters scattered on the retina, as multiple instances widely distributed or in larger numbers in one or more clusters.

In the context of retinal diseases, for example, there are systems and protocols in use for grading the severity or state of the retinal disease (see, e.g., DR Guidelines Expert Working Party Members. The royal college of ophthalmologists, diabetic retinopathy guidelines, 2012). Usually, a clinician provides a summarized estimate of lesion distribution, for example by determining whether or not lesions are present in the macula. In addition, the presence of lesions inside or outside the macula, defined as a circle of fixed diameter centred on the fovea, may be used in grading of diabetic maculopathy (oedema). This can be made by a quick visual assessment by the clinician with or without a measurement aid. In addition, a comparison to standard photographs may be used to assess a lesion number in DR. Such lesions are thus seen to vary in number according to the severity or state of the disease.

SUMMARY

Automated detection of diseases in medical images may be based on identifying a relationship between lesion distribution and a current and/or future status of a disease. Individual lesions may be recorded across a large number of patients and a distribution of lesions may be parametrised, for example in population screening. This may lead to alternative screening protocols based on parameters of a distribution of dot or otherwise shaped lesions in the human body.

However, the number of lesions in a medical image is not a fixed number, and so between subjects there would be a varying (not fixed) number of lesion statistics. These statistics would be of value for training purposes in order to associate or correlate signatures of lesion distributions with disease states or pathological conditions and/or to indicate or predict an unknown disease state.

Typical automated classifiers, such as an artificial neural network, a linear model, a support vector machine or a K-nearest neighbour classifier, require fixed data arrays as input. Therefore, an attempt to train an automated classifier, e.g. based on one or more machine-learning algorithms, in order to predict or determine a disease state or pathological condition based on lesion statistics is problematic in the case of a variable (not fixed) number of data. Although there are ways to provide a summary of the variable number of data, for example by reducing the lesion data to a count of the number of lesions and thus to provide a fixed number of data as input into a machine-learning algorithm, such a summary would omit information relating to a spatial distribution across the medical image and/or relating to the way the lesions are associated with one another.

Accordingly, It would be useful to avoid the requirement of fixed sized data arrays for the training of automated classifiers in connection with the problem of omitting information as to a spatial distribution of lesions. A solution may lead to improved clinical protocols based on parameters of lesion distribution in the human body.

In view of the limitations discussed above, the present inventors have devised, in accordance with a first example aspect herein, a computer-implemented method of determining a pathologic condition from a medical image of a portion of a subject captured using a medical imaging system. The method comprises the steps of acquiring a plurality of lesion locations in the medical image; applying a clustering algorithm to the plurality of lesion locations in order to identify at least one lesion cluster and corresponding lesion cluster data; categorizing each of the at least one lesion cluster into one of a set of predetermined categories based on the determined lesion cluster data; applying at least one function to the lesion cluster data with regard to each category of the set of predetermined categories, wherein the at least one function provides a fixed number of data outputs; and determining a pathologic condition from the medical image by processing the fixed number of data outputs of each category of the set of predetermined categories based on a classification algorithm trained on image data defining medical images of the portion of a plurality of subjects.

The present inventors have further devised, in accordance with a second example aspect herein, a computer program which, when executed by a computer, causes the computer to perform the method according to the first example aspect herein.

The present inventors have further devised, in accordance with the third example aspect herein, an apparatus for determining a pathologic condition from a medical image of a portion of a subject captured using a medical imaging system. The apparatus comprises an acquiring module configured to acquire a plurality of lesion locations in the medical image and a categorizing module configured to apply a clustering algorithm to the plurality of lesion locations in order to identify at least one lesion cluster and corresponding lesion cluster data; categorize each of the at least one lesion cluster into one of a set of predetermined categories based on the determined lesion cluster data; and apply at least one function to the lesion cluster data with regard to each category of the set of predetermined categories, wherein the at least one function provides a fixed number of data outputs. The apparatus further comprises a determining module configured to determine a pathologic condition from the image by processing the fixed number of data outputs of each category of the set of predetermined categories based on a classification algorithm trained on image data defining medical images of the portion of a plurality of subjects.

BRIEF DESCRIPTION OF THE DRAWINGS

Embodiments of the invention will now be explained in detail, by way of non-limiting examples only, with reference to the accompanying figures described below. Like reference numerals appearing in different ones of the figures can denote identical or functionally similar elements, unless indicated otherwise.

DETAILED DESCRIPTION OF EXAMPLE EMBODIMENTS

Example embodiments herein will now be described in detail with reference to the accompanying drawings.

Figure 1:
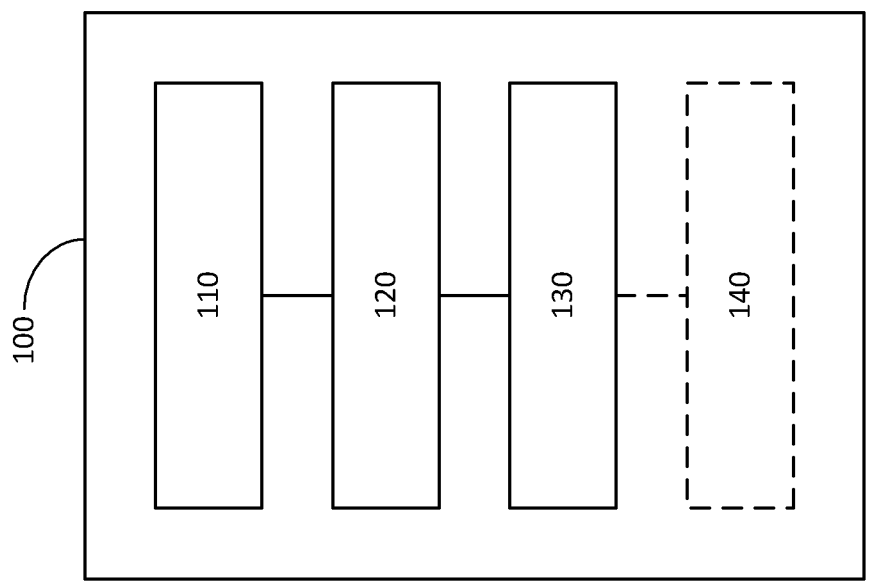
FIG. 1 is a schematic illustration of an apparatus for determining a pathologic condition from a medical image of a portion of a subject captured using a medical imaging system, according to an example embodiment herein.
Figure 4:
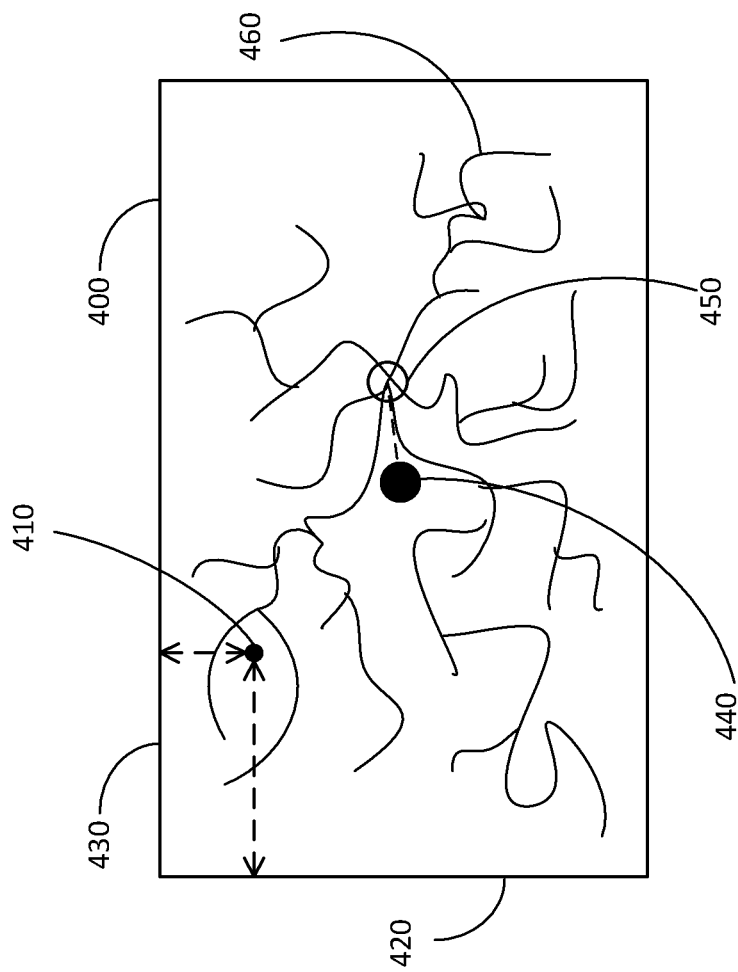
FIG. 4 is a schematic illustration of a medical image of a portion of the retina of a subject captured using a scanning laser ophthalmoscope, SLO, in which the location of the lesion 410 is defined in a two-dimensional image-based coordinate system, in accordance with an example embodiment herein.
Figure 5A:
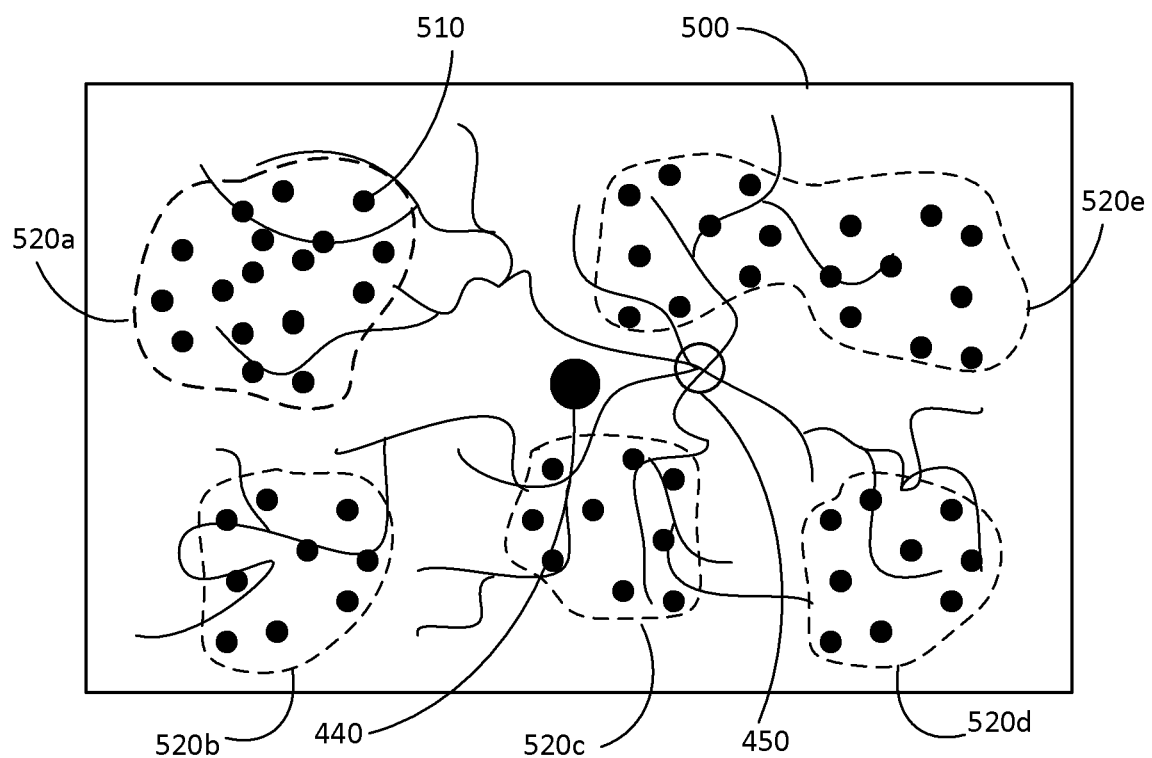
FIG. 5(a) is a schematic illustration showing a medical image, in which lesions are present, to which a clustering algorithm has been applied, in accordance with a first example embodiment herein.
Figure 5B:
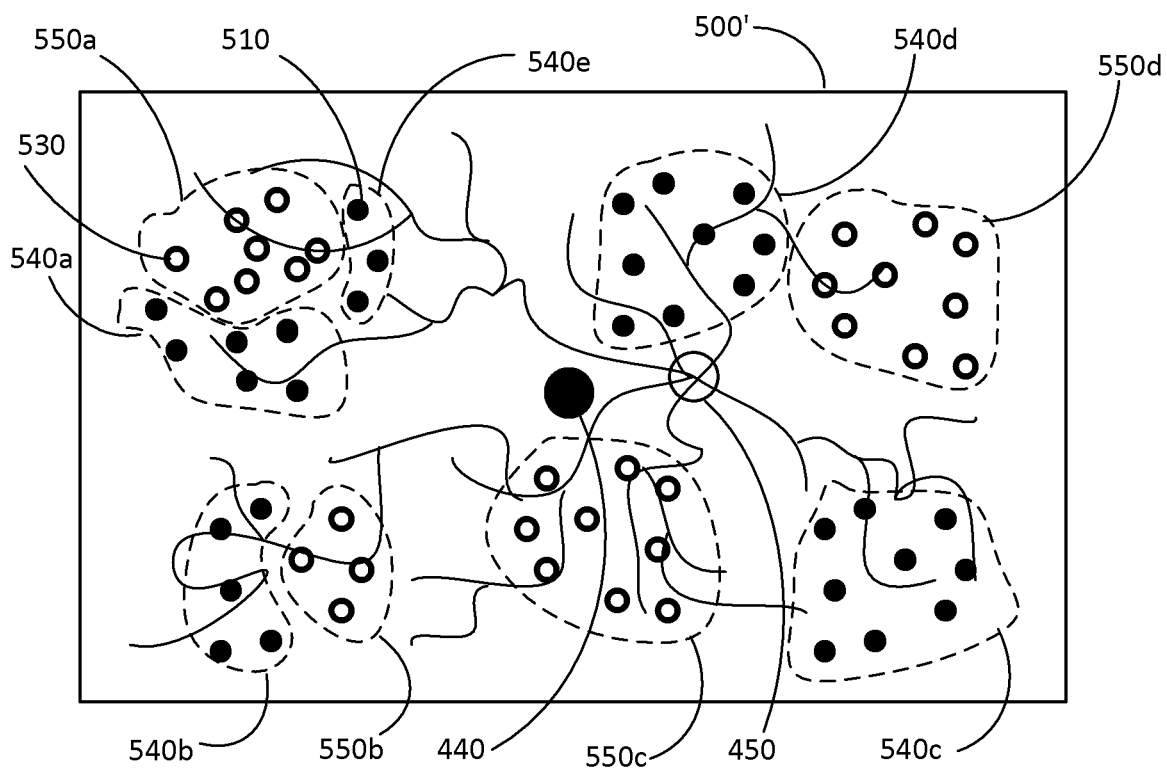
FIG. 5(b) is a schematic illustration showing a medical image, in which lesions are present, to which a clustering algorithm has been applied, in accordance with a second example embodiment herein.

FIG. 1 is a schematic illustration of an apparatus 100 for determining a pathologic condition from a medical image 400, 500, 500'(as shown in FIGS. 4, 5(a), 5(b), respectively) of a portion of a subject captured using a medical imaging system 350 (shown in FIGS. 7 and 8), according to an example embodiment herein.

Figure 7:
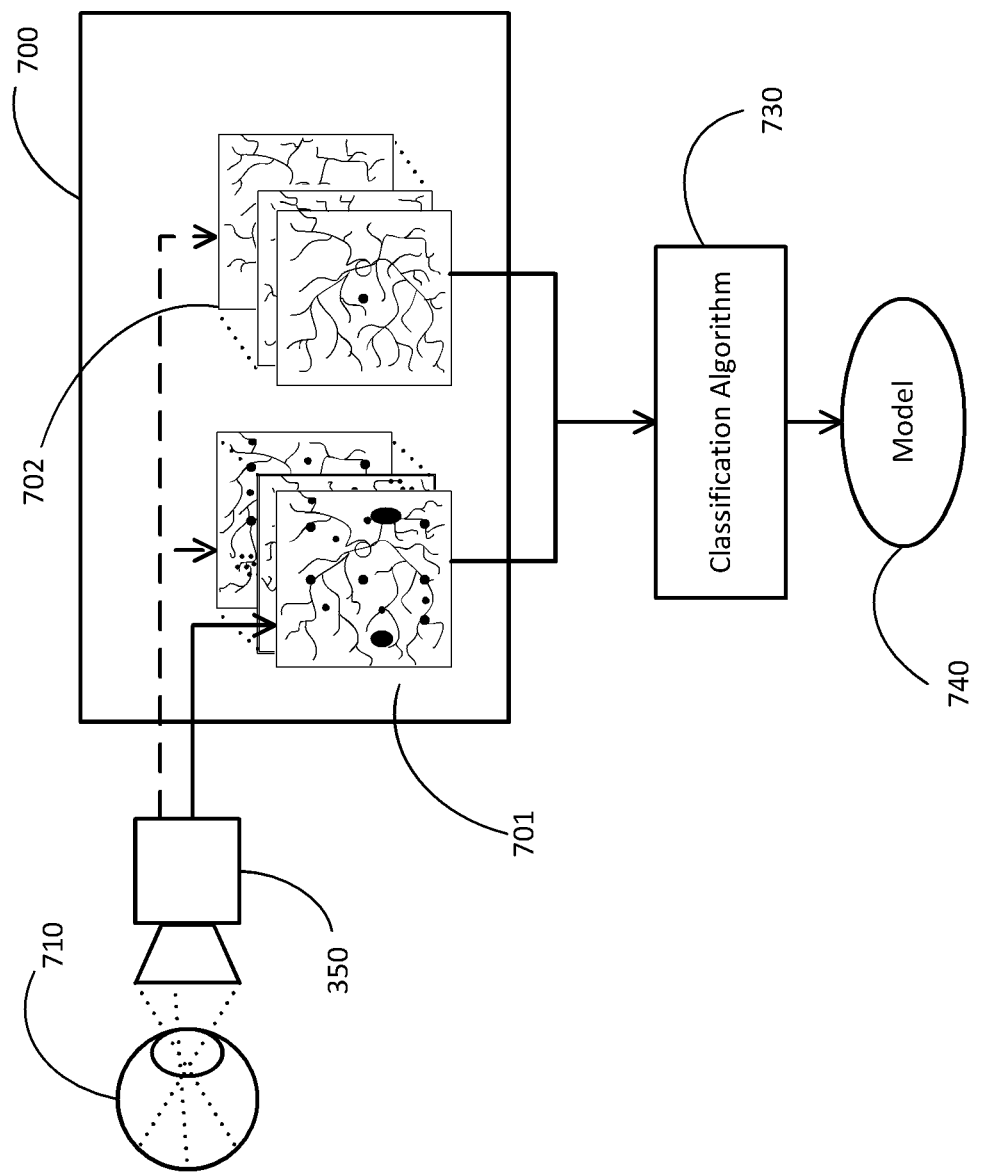
FIG. 7 is a schematic illustration showing how a classification algorithm may be trained on image data defining medical images of the portion of a plurality of subjects, in accordance with a first example embodiment herein.

The apparatus 100 comprises an acquiring module 110, a categorizing module 120, and a determining module 130. The acquiring module 110 is configured to acquire a plurality of lesion locations in the medical image 400, 500, 500'. The categorizing module 120 is configured to apply a clustering algorithm to the plurality of lesion locations in order to identify at least one lesion cluster and corresponding lesion cluster data, categorize each of the at least one lesion cluster into one of a set of predetermined categories based on the determined lesion cluster data, and apply at least one function to the lesion cluster data with regard to each category of the set of predetermined categories, wherein the at least one function provides a fixed number of data outputs. The determining module 130 is configured to determine a level of pathology present in the image by processing the fixed number of outputs of each category of the set of predetermined categories using a classification algorithm 730 (as shown in FIG. 7) trained on image data defining medical images 701, 702 (as shown in FIG. 7) of the portion of a plurality of subjects.

The subject may be a human. The portion of the subject, of which a medical image is captured by the medical imaging system 350, may be any anatomical portion (exterior or interior to the body) of the subject for which a pathology or disease of that portion may present as lesions that are visible in, or otherwise deducible from, a medical image of that portion.

A lesion may be, in one non-limiting example, a small, dot-like abnormality that is caused by a pathology, and would not be present in a similarly-acquired image of a healthy subject. Lesions, i.e. any damage or abnormal change in tissue, may be caused by diseases or trauma, for example, and may be a dot-like or other shaped abnormality.

The medical image 400, 500, 500' may, as in the present embodiment, be a ultra-wide field retinal image captured using a scanning imaging system in the exemplary form of a scanning laser ophthalmoscope (SLO), which is configured to acquire images of the retina of a subject's eye. The SLO of the present example embodiment is configured to capture autofluorescence (AF) images (it may be configured to capture multi-wavelength reflectance images or images from other fluorescence modes), although it may alternatively or additionally be configured to acquire one or more other types of images. The SLO may, for example, be an ultra-wide field SLO (UWF-SLO) capable of generating an ultra-wide field image of up to 80% of a retinal surface.

Alternatively and more generally, the medical image may be an ocular image captured using any ocular imaging system (e.g., formed by system 350) other than an SLO, that is suitable for imaging the retina or any other selected portion (for example a portion of the anterior segment of the eye, or a portion of the posterior segment of the eye) of the eye.

The ocular imaging system may, for example, be a fundus camera. Alternatively, the ocular imaging system may be of another imaging modality, for example an optical coherence tomography (OCT) scanner, in which case the image processing techniques described herein are applicable to the tomographic images acquired by the OCT scanner. As a further alternative, the ocular imaging system may be a combined SLO-OCT scanner, in which case the image processing techniques described herein are applicable to both the SLO retinal scans and the OCT scans acquired by the combined SLO-OCT scanner. The imaging modality of the ocular imaging system may, for example, take one of the many different forms known to those versed in the art, including OCT, colour fundus photography, fluorescein angiography (FA), indocyanine green angiography (ICG) and autofluoresence (AF), among others.

By way of further alternative, the medical image may be an image of the lungs captured using an x-ray imaging system, a computed tomography (CT) imaging system, or a low dose CT (LDCT) imaging system. Alternatively, the medical image may be an image of the brain captured using a magnetic resonance imaging (MRI) imaging system. By way of still further alternative, the medical image may be an image of the skin captured using a camera.

Accordingly, the medical imaging system 350 may be any of those discussed above, or any other medical imaging system suitable to image a portion of a subject (such as, for example, a portion of the retina, the anterior segment of the eye, the posterior segment of the eye, the lungs, the brain, or the skin).

Figure 2:
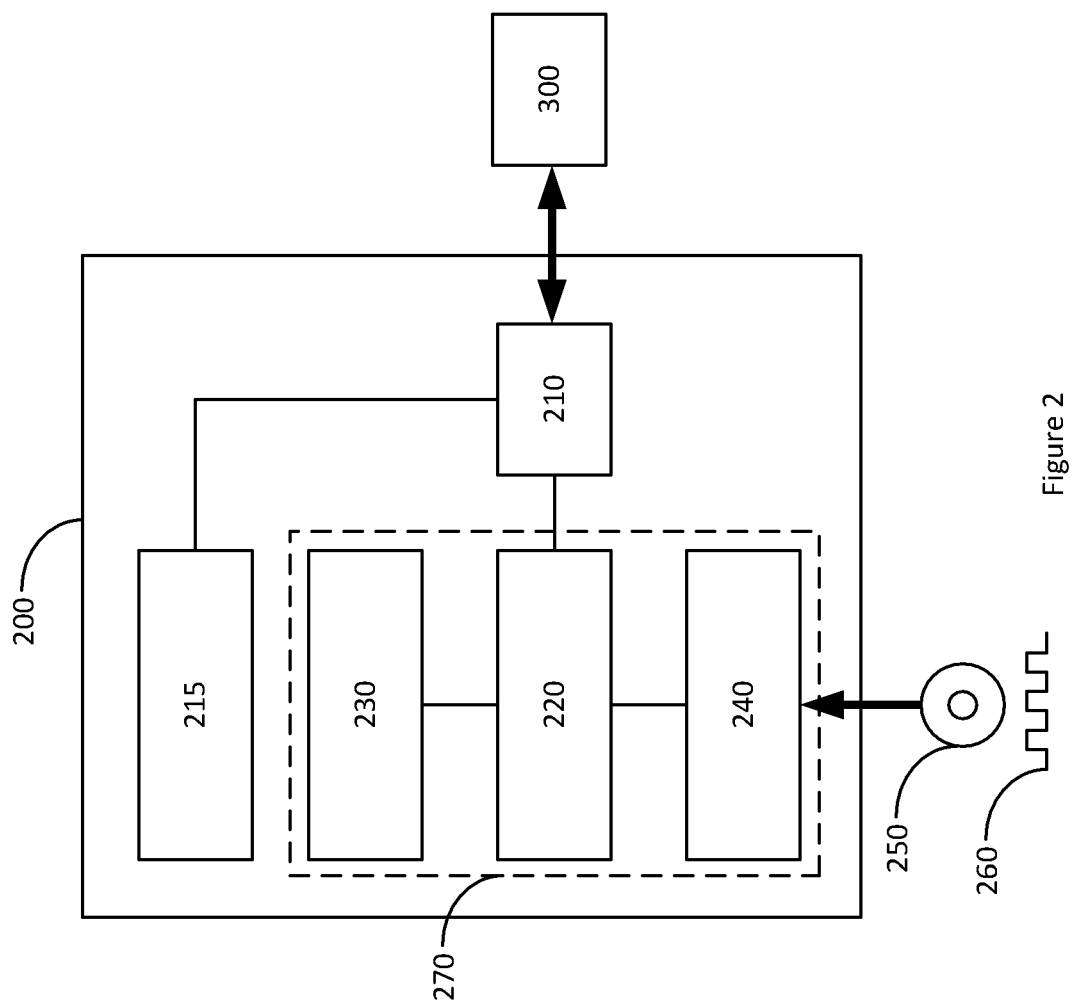
FIG. 2 is a block diagram illustrating an example signal processing hardware configuration of the apparatus of FIG. 1, according to an example embodiment herein.

The acquiring module 110 is configured to acquire a plurality of lesion locations in the medical image 500 (as shown in FIG. 5(a)). The acquiring module 110 may, as in the present embodiment, be configured to acquire the plurality of lesion locations in the medical image from an automated lesion detector 300 (as shown in FIG. 2). In particular the set of lesion locations may be produced by and subsequently acquired from the automated lesion detector 300.

Automated lesion detectors are known (e.g., Bhaskaranand et al. "Automated diabetic retinopathy screening and monitoring using retinal fundus image analysis. Journal of diabetes science and technology, 10(2):254-261, 2016; Fleming et al. "Automated microaneurysm detection using local contrast normalization and local vessel detection". IEEE transactions on medical imaging, 25(9):1223-1232, 2006), for example in terms of a software-based module whose input is a medical image, such as medical image 400, 500, 500'. The automated lesion detector 300 processes the medical image to determine or identify a set of locations or small regions and may also determine a set of properties associated with the determined or identified location/region. Here, each such location or small region may be a location of a pathological abnormality or a lesion. In one example embodiment herein, the automated lesion detector 300 can operate according to at least one of the aforementioned publications, each of which is incorporated by reference herein in its entirety, as if set forth fully herein.

Furthermore, the medical image data input to the automated lesion detector 300 may, as in the present example embodiment, define a two-dimensional image, or it may alternatively define a three-dimensional image of the imaged portion of the eye. The received image data may be provided in any suitable format (whether compressed or uncompressed) known to those skilled in the art. The output of the automated lesion detector 300 (that is, the output of processing the medical image) is then a data set of unfixed size (undefined data quantity), where the data represents a set of lesions, each of which may include an array of properties. In particular, prior to the processing of a particular medical image using the automated lesion detector 300, the size of the set of data (e.g. the number of lesions) is unknown and cannot be determined. Furthermore, the size of the data set is unfixed in that the number of lesions that may be determined by the automated lesion detector 300 is not fixed or limited to a certain range. That is, input to the apparatus 100 of FIG. 1 may be the output of an automated lesion detector 300, which is a set of locations determined to be the likely locations of pathological abnormalities or lesions within the body and properties of these detected lesions.

The automated lesion detector 300 may, as in the present embodiment, be configured to obtain an input medical image, such as medical image 400, 500, 500' directly from the medical imaging system 350 by any suitable means known to those versed in the art. Alternatively, the automated lesion detector 300 may be configured to obtain a previously captured and stored medical image (e.g. by reading from a storage medium such as a CD or hard disk, or receiving via a network such as the Internet) after it has been captured by the medical imaging system 350 or produced by other means. By way of further alternative, the automated lesion detector 300 may be provided as part of the medical imaging system 350.

The acquiring module 110 may be configured to acquire a plurality of lesion locations in the medical image by any suitable means known to those versed in the art. For example, the acquiring module 110 may receive the plurality of lesion locations from the automated lesion detector 300 via a direct communication link (which may be provided by any suitable wired or wireless connection, e.g. a Universal Serial Bus (USB) or a Bluetooth™ connection), or an indirect communication link (which may be provided by a network comprising a Local Area Network (LAN), a Wide Area Network (WAN) and/or the Internet). Furthermore, the plurality of lesion locations may be acquired by the acquiring module 110 acquiring (e.g. by reading from a storage medium such as a CD or hard disk, or receiving via a network such as the Internet) such a plurality of lesion locations after it has been output by the automated lesion detector 300 or produced by other means.

Alternatively, the acquiring module 110 may include an automated lesion detector 300, as described above. As such, the acquiring module 110 of the apparatus of FIG. 1 may be configured to acquire a plurality of lesion locations in the medical image by receiving the medical image data defining the medical image and processing the medical image data in order to determine the location of each of a plurality of lesions in the medical image by any suitable means known in the art.

Furthermore, the plurality of lesion locations may be received by the acquiring module 110 (and may furthermore subsequently be processed to determinate level of pathology present in the medical image, as described below) concurrently with the generation of the plurality of lesion locations by the automated lesion detector 300, i.e. the plurality of lesion locations may be acquired "on the fly". However, in the present example embodiment, and for the purposes of this description, the acquiring module 110 is configured to acquire in the medical image a plurality of lesion locations before the categorizing module 120 begins to process this plurality of lesion locations.

In embodiments like the present illustrated embodiment, where the apparatus 100 further comprises a display control signal generator 140, the display control signal generator 140 may be arranged to generate display control signals for controlling a display device (as shown at 215 in FIG. 2), such as an LCD screen or other type of visual display unit, to display the locations of the plurality lesions and/or the at least one cluster identified in the medical image of the portion of the subject, and/or a representation of the determined level of pathology.

FIG. 2 is a schematic illustration of a programmable signal processing hardware 200, which may, as in the present example embodiment, be configured to function as the apparatus 100 of FIG. 1. The programmable signal processing hardware 200 comprises a communication interface (I/F) 210 for receiving data indicative of the plurality of lesion locations described above (e.g., from automated lesion detector 300), and, optionally, for outputting display control signals for controlling the display device 215 to display both the locations of the plurality lesions and/or the at least one cluster identified in the medical image of the portion of the subject, and/or a representation of the determined level of pathology. The signal processing apparatus 200 further comprises a processor (e.g. a Central Processing Unit, CPU, or Graphics Processing Unit, GPU) 220, a working memory 230 (e.g. a random access memory) and an instruction store 240 storing a computer program comprising the computer-readable instructions which, when executed by the processor 220, cause the processor 220 to perform various functions including those of the categorizing module 120, determining module 130 and, optionally, the display control signal generator 140 described above. The instruction store 240 may comprise a ROM (e.g. in the form of an electrically-erasable programmable read-only memory (EEPROM) or flash memory) which is pre-loaded with the computer-readable instructions. Alternatively, the instruction store 240 may comprise a RAM or similar type of memory, and the computer-readable instructions of the computer program can be input thereto from a computer program product, such as a non-transitory, computer-readable storage medium 250 in the form of a CD-ROM, DVD-ROM, etc. or a computer-readable signal 260 carrying the computer-readable instructions. In any case, the computer program, when executed by the processor, causes the processor to execute at least one of the methods of processing a medical image data of a portion of a subject captured using a medical imaging system to determine a level of pathology present in a medical image defined by the medical image data described herein. It should be noted, however, that the apparatus 100 may alternatively be implemented in non-programmable hardware, such as an application-specific integrated circuit (ASIC).

In the present example embodiment, a combination 270 of the hardware components shown in FIG. 2, comprising the processor 220, the working memory 230 and the instruction store 240, is configured to perform functions of the categorizing module 120 and determining module 130, which functions will now be described in further detail below. In embodiments like the present illustrated embodiment, where the apparatus 100 comprises a display control signal generator 140, the functionality of this optional component also be provided by the combination 270 of the hardware components, together with the communication I/F 210.

As will become more apparent from the following description of the operations performed by the apparatus 100 of the present example embodiment, the apparatus of FIG. 1 overcomes the requirement of a fixed sized data arrays for the training of automated classifiers in connection with the problem of omitting information as to a spatial distribution of lesions, thereby allowing the determining module to determine a level of pathology present in the medical image by processing data derived from the plurality of lesion locations using one or more classification algorithms, as an example of an automated classifier.

Figure 3:
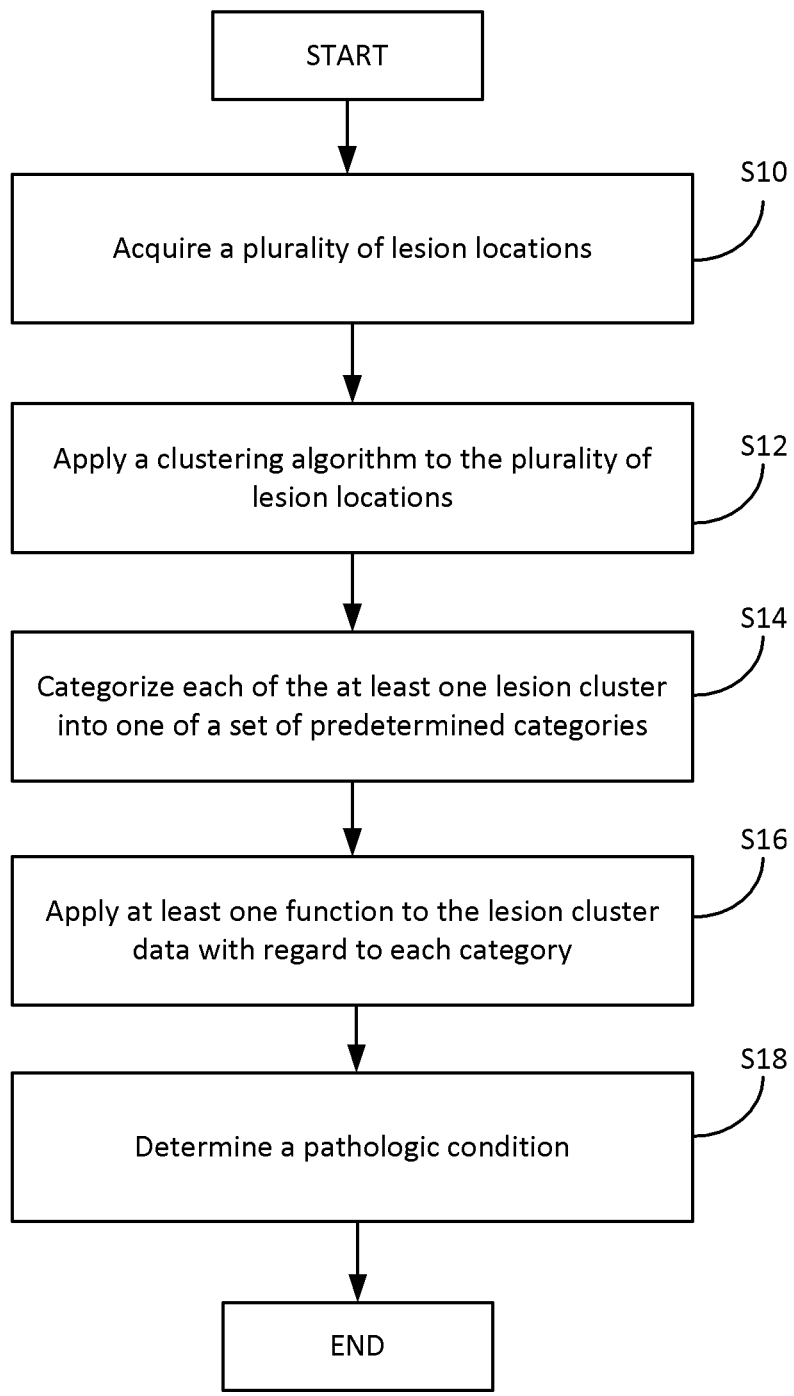
FIG. 3 is a flow diagram illustrating a process by which the apparatus of FIG. 1 processes medical image data to determine a pathologic condition, in accordance with an example embodiment herein.

FIG. 3 is a flow diagram illustrating a process by which the apparatus 100 of FIG. 1 processes medical image data to determine a pathologic condition, in accordance with and example embodiment herein.

In process step S10 of FIG. 3, the acquiring module 110 of FIG. 1 acquires a plurality of lesion locations in a medical image 500.

As discussed above, the acquiring module 110 may be configured to acquire the plurality of lesion locations by any suitable means known in the art. In the present embodiment the acquiring module 110 is configured to acquire the plurality of lesion locations from an automated lesion detector 300.

The acquiring module 110 may, as in the present embodiment, acquire a unique, respective location for each lesion of the plurality of lesions. The location of each lesion may be, by way of example, the location of a centroid or a centre of mass of that lesion, the location of a vertex of a shape (e.g. a rectangle, ellipse or circle) of a predetermined size containing that lesion, or any other suitable location indicative of the position of the lesion. The location of each lesion may also be a set of coordinates defining the area or extent of each lesion (e.g. vertex of a shape (e.g. a rectangle, ellipse or circle) containing that lesion, coordinates indicating a longest dimension of that lesion, etc.)

The locations may be defined in any suitable coordinate system. By way of example, each location of the plurality of lesion locations may be defined in a two-dimensional image-based coordinate system. By way of example, FIG. 4 is a schematic illustration of a medical image 400 of a portion of the retina of a subject captured using a scanning laser ophthalmoscope, SLO, in which the location of a single exemplary lesion 410 is defined in a two-dimensional (image-based) coordinate system of the medical image 400, in accordance with an example embodiment herein. In FIG. 4, the location of lesion 410 is defined by an x-coordinate indicative of the number of pixels between a specified pixel (in this embodiment, the centre pixel of lesion 410) and the left edge 420 of the image 400, and a y-coordinate indicative of the number of pixels between the specified pixel and the top edge 430 of the image 400.

In the example of FIG. 4, a single lesion 410 is illustrated. However, in alternative embodiments, multiple lesions may be present in medical images, such as medical image 400. Furthermore, in the example of FIG. 4, the x-coordinate is indicative of a number of pixels between the specified pixel (related to the lesion) and left edge 420 of the image 400 and the y-coordinate is indicative of a number of pixels between the specified pixel and the top edge 430 of the image 400. In alternative embodiments, the x-coordinate may be indicative of a number of pixels between a specified pixel and the right edge of the medical image 400 and the y-coordinate may be indicative of a number of pixels between specified pixel and the bottom edge of the medical image 400.

Alternatively, each location of the plurality of lesion locations may, as in the present embodiment, be defined in a two-dimensional coordinate system or a three-dimensional coordinate system adapted to the portion of the subject being imaged. Such a coordinate system may be referred to as a normalised coordinate system (NCS). A NCS can be defined using any suitable combination of relevant factors. The choice of factors taken into consideration may make a compromise between complexity and what is known or assumed about a factor's relevance to disease or its clinical effectiveness.

In particular, in a case where the portion of the subject being imaged is a portion of the retina, as in the present embodiment, a coordinate system based on pixel row and column in an image may not take into account any of the following factors: the approximately spherical nature of the retinal surface; the likely oppositely oriented physiology of left and right eyes; changes in orientation of the eye caused by gaze and head inclination; scaling caused by image magnification or the size of relevant anatomy. Accordingly, in a case where the portion of the subject being imaged is a portion of the retina, it may be preferable to define a coordinate system which takes these factors into account.

A coordinate system that takes into account one or more of these factors will be referred to as a retinal NCS (RNCS).

[Accounting for Spherical Shape]

A RNCS can be defined in terms of spherical coordinates such as azimuth and elevation relative to a point on the retina. A mapping is required between pixel coordinates in the image and azimuth and elevation and this could be obtained from a suitable mapping algorithm by an optical modelling software for the imaging system.

[Accounting for Orientation]

A natural location for the origin of the RNCS is the centre of the fovea 440 (as shown in FIG. 4), this being the centre of gaze which is usually under the subject's control. The centre of the optic nerve head, ONH, 450 (as shown in FIG. 4) is also a natural location for the origin of the RNCS since the eye's vasculature 460 (as shown in FIG. 4) and retinal nerves radiate from this structure. This accounts for changes in the eye's orientation in two axes in a three-dimensional space.

A natural means for accounting for the orientation of the eye in the third axis of the three-dimensional space is to use centres of both the fovea 440 and optic nerve head 450. A straight line in the image through these points can be used as the nominally horizontal axis since this line is unlikely to be more than 20 degrees away from horizontal.

[Accounting for Laterality]

The positive direction for the horizontal axis of the RNCS can be opposite for left and right eyes. This allows the RNCS to take into account the assumption that there is oppositely oriented physiology of left and right eyes.

[Accounting for Scale]

The scale of the image could be obtained in multiple ways using retinal anatomy. After the image scale is assessed, and quantified, the RNCS can be scaled so that it matches the retinal anatomy. As with laterality, it is an assumption that physiological scale (that is, the actual scale of the eye) matches observed anatomical scale (that is, the scale in the images portion of the eye). Although the size of the observed anatomy is dependent on image magnification and on actual anatomical size it is assumed that both contribute in the same way to the distribution of lesions in the image. The following methods may be used to assess scale:

1. The size of the ONH 450.
2. The distance between the centres of the fovea 440 and the ONH 450.
3. The distance between the main vascular arcades and the fovea 440. This could be evaluated by finding the distance from the fovea 440 to peaks in a smoothed profile of the retinal vasculature or between peaks in the smoothed profile, wherein the profile extends from the fovea 440 in a direction that does not intersect the optic nerve head 450.

Methods are available in a fully automated system to detect locations of the centre of the fovea, the centre of the ONH 450, the outline of the ONH 450, and the vasculature 460. Therefore, the assignment of a RNCS as above can be performed automatically. By correctly selecting the direction of the profile of the retinal vasculature, described in relation to method 3 above, so that the direction is orthogonal to a line between the centres of the fovea 440 and the ONH 450, the assessments of scale using the distances 2 and 3 above may be rendered orthogonal. Accordingly, these two methods of assessing scale may be used in combination to separately scale the (nominally) horizontal and vertical axes of the RNCS.

In the preceding example, a three-dimensional normalised coordinate system adapted to retinal imaging is discussed. However, in alternative embodiments, a coordinate system may be defined that is adapted to other portions of the subject being imaged such as, for example, the lungs, the brain, the skin (for various portions of the body), the anterior segment of the eye and the posterior segment of the eye.

By way of example, in a case where the portion of the subject being imaged is a portion of the brain, two types of NCS, known as Talairach coordinates (Lancaster et al., "Automated talairach atlas labels for functional brain mapping", Human brain mapping, 10(3):120-131, 2000) and MNI stereotaxic space (Tzourio-Mazoyer et al., "Automated anatomical labeling of activations in spm using a macroscopic anatomical parcellation of the mni mri single-subject brain", Neuroimage, 15(1):273-289, 2002), are commonly used in brain imaging. Talairach coordinates is defined by making two anchors, the anterior commissure and posterior commissure, and making them lie on a horizontal line. Both coordinate systems are intended to account for individual differences in the size and shape of the brain.

By way of further example, in a case where the portion of the subject being imaged is a portion of the lungs (pulmonary imaging), while there is less usage of NCS based on anatomical features, a NCS based on normalised orientation of the pleural surface bas been described to create a more consistent description of the location of detected lung nodules (Jirapatnakul at al., "Segmentation of juxtapleural pulmonary nodules using a robust surface estimate", Journal of Biomedical Imaging, 2011:15, 2011).

In one example embodiment herein, a NCH may be implemented according to at least one of the aforementioned publications, each of which is incorporated by reference herein in its entirety, as if set forth fully herein.

Optionally, the acquiring module 110 may, as in the present embodiment, further acquire, as a lesion property, at least one of the type of lesion, a lesion area, a lesion volume, a lesion shape complexity, a lesion intensity, and a lesion colour for each of the plurality of lesion locations in the medical image. That is, the acquiring module 110 may acquire at least one lesion property of a lesion associated with each of the plurality of lesion locations.

The acquiring module 110 may, as in the present embodiment, be configured to acquire the lesion property for each plurality of lesion locations from an automated lesion detector 300. By way of alternative, in a case where the acquiring module 110 is configured to acquire a plurality of lesion locations in the medical image by receiving the medical image data defining the medical image and processing the medical image data in order to determine the location of each of a plurality of lesions in the medical image, the acquiring module 110 may be further configured to process the medical image data in order to determine at least one lesion property for each of the plurality of lesion locations.

A type of a lesion may be, for example, a disease or pathology causing lesion. By way of example, with regard to the lungs, lung cancer may present as benign and malignant pulmonary nodules (lesions). With regard to the brain, multiple sclerosis, lupus, and Alzheimer's disease may result in lesions that are visible using, for example, MRI. With regard to retina, diseases such as diabetic retinopathy and age-related macular degeneration, AMD, may result in small focal lesions. The disease identified as causing a lesion may, therefore, be considered a type of the lesion.

Furthermore, there exist numerous varieties of skin lesions, many of which can be characterised according to their distribution. Several terms may be used to describe how lesions are spatially distributed. They may be isolated (solitary or single) or multiple. The localisation of multiple lesions in certain regions helps diagnosis, as skin diseases tend to have characteristic distributions. Descriptive terms include, acral (relating to or affecting the distal extremities), following Blaschko lines (following roughly linear, segmental pattern), dermatomal (lesions confined to one or more segments of skin innervated by a single spinal nerve and generalised (lesions distributed randomly over most of the body surface area or within an anatomical region), and herpetiform (solid papules within a cluster). Accordingly, in the case for the portion of the subject is a portion of the subject's skin, the type of lesion may refer to one of these terms.

Alternatively, a type of lesion may be whether or not the lesion has a particular quality, for example being circinate, exudate, flat, smooth, spiculated, or any other quality that may be of interest to medical practitioner or other user of the apparatus 100.

A lesion area or a lesion volume may be defined in terms of pixels or any other coordinate system. In particular, a lesion area or a lesion volume could be the area or volume occupied by a lesion in one of the coordinate systems discussed above or may be an estimate of true area or volume in the human body. In estimating or calculating a lesion area or lesion volume, it may be assumed that lesions are small enough that each individual lesion occupies a region in the body surface that is small enough to be considered as a flat plane.

A lesion shape complexity may be defined in any suitable manner known in the art. By way of example, a lesion shape complexity may be defined as the ratio of a perimeter of the lesion to the area of the lesion.

A lesion intensity may be an average intensity value of the pixels of the lesion in the medical image or a contrast value between the pixels of the lesion and the surrounding areas in the medical image. A lesion colour may be defined in any suitable colour representation system known in the art (for example, RGB, HSV, CYMK, etc.).

In process step S12 of FIG. 3, the categorizing module 120 of the apparatus 100 of FIG. 1 applies a clustering algorithm to the plurality of lesion locations in order to identify at least one lesion cluster and corresponding lesion cluster data.

The output of the clustering step is a set of lesion clusters. Each lesion cluster represents a subset of the lesions which were input to the clustering algorithm. These subsets are usually non-intersecting. Algorithms for cluster analysis might be applied to the locations of lesions to yield quantified information that characterises the visually observed clustering of the lesions in acquired medical images.

By way of example, FIG. 5(a) is a schematic illustration showing a medical image 500, in which lesions 510 are present, to which a clustering algorithm has been applied, in accordance with a first example embodiment herein. In the example of FIG. 5(a), the medical image 500 is an image of a portion of the retina of a subject captured using a scanning laser ophthalmoscope, SLO, but may be any form of medical image in which lesions are present (such as, for example, a medical image of a subject's brain, lungs and skin). As shown in FIG. 5(a) the output of the clustering algorithm is a set of lesion clusters 520a, 520b, 520c, 520d and 520e, which are indicated using dashed lines.

It can be observed that, in the example of retinal lesions 510, though seeming to form at random locations on the retina these are often clustered over smaller or larger regions. In the retina, there are a few examples where lesion clusters correspond to clinical practice:

Circinate exudate clusters in diabetic retinopathy, DR;
Macular drusen in advanced macular degeneration, AMD.

In an alternative embodiment, in a case where the acquiring module 110 is configured to acquire a lesion property for each of the plurality of lesion locations in the medical image, the categorizing module 120 may be further configured to apply the clustering algorithm to the lesion property data. That is, in addition to the plurality of lesion locations, the clustering algorithm may receive the lesion property of each of the lesion locations as an input. By way of example, a parameter or any other suitable factor of the clustering algorithm may be selected based on the lesion property for each of the plurality of lesion locations. Alternatively, the lesion property for each of the plurality of lesion locations may be used by the clustering algorithm to influence or control clustering of the lesion locations in any suitable way.

By way of further alternative, in a case where the acquiring module 110 is configured to acquire a lesion property for each of the plurality of lesion locations in the medical image, the categorizing module 120 may be configured to apply the clustering algorithm with regard to the plurality of lesion locations having the same lesion property.

FIG. 5(b) is a schematic illustration showing a medical image 500', in which lesions 510, 530 are present, to which a clustering algorithm has been applied, in accordance with a second example embodiment herein. In the embodiment of FIG. 5(b), a type of lesion has been acquired by the acquiring module 110, as a lesion property, for each of the plurality of lesion locations in the medical image 500'. The clustering algorithm is applied with regard to a first plurality of lesion locations of lesions 510 having the same lesion property, that is, lesions 510 of a same first type. The output of the clustering algorithm is a set of lesion clusters 540a, 540b, 540c, 540d and 540e of the same lesion type, which are indicated using dashed lines.

Additionally, in the example of FIG. 5(b), the clustering algorithm is then applied with regard to a second plurality of lesion locations of lesions having the same lesion property, that is, lesions 530 of a same second type. In this case, the output of the clustering algorithm is a set of lesion clusters 550a, 550b, 550c, and 550d of the same lesion type, which are indicated using dashed lines.

In the example of FIG. 5(b), the same lesion property is a type of lesion. Alternatively, the same lesion property may be, for example, any one of a lesion area, a lesion volume, a lesion shape complexity, a lesion intensity, and a lesion colour.

The number of clusters to be determined by the clustering algorithm is not fixed. Over the population of people with a particular disease, lesions may form in a wide variety of patterns. There may be a single cluster or multiple clusters. Lesions vary in size and some of this size variation contributes to the visual impression of density or sparsity and hence also to the observed clustering. A cluster may have a generally round globular shape or may have more complex topology such as in the case of circinate exudates, or, in the example of retinal imaging, macular drusen form clusters that avoid yet surround the fovea. In these cases the cluster may be more sparse centrally than towards its periphery giving the impression of a ring-shaped cluster.

There are many algorithms for analysis and detection of clusters present in medical image data. A suitable clustering algorithm may cope with some or all of the above factors.

By way of example, the clustering algorithm applied by the categorising module 120 may, as in the present embodiment, not require, as input, an indication of a number of clusters. Some clustering algorithms, such as k-means clustering, require prior specification of the number of clusters as this is used as an input. In order to allow for the range of presentations of disease across the population, a clustering algorithm that does not make prior assumption about the form of lesion clustering should preferably be used instead of, for example, k-means clustering, which requires such an assumption.

In this context, a clustering algorithm that does not make prior assumption about the form of lesion clustering may, as in the present embodiment, comprise at least one of a density-based spatial clustering of applications with noise (DBSCAN) algorithm and applying a threshold to a bandpass filtered map of the plurality of lesion locations. Alternatively, any other suitable clustering algorithm known in the art may be used.

In bandpass filter clustering, a band pass filter is applied to a map of objects (in this context, a map of a plurality of lesion locations) to be clustered. Let L be a map of the acquired plurality of lesion locations to be clustered. Then band pass filtered map, $L_{bpf}$, can be represented by:

$$L_{bpf} = (L \cdot G(a))/(L \cdot G(b)) - 1$$

Where 'o' represents convolution, G(s) represents a 2-dimensional Gaussian function with standard deviation s and a and b (a>b) control the upper and lower roll off points of the band pass filter.

The resulting band pass filtered map, $L_{bpf}$, can be thresholded, for example by using a hysteresis to form a map of clusters. For example, thresholding based on hysteresis may be represented by:

$$L_{cluster} = rec(L_{bpf}, t_1, t_2)$$

using rec to represent morphological reconstruction (https://uk.mathworks.com/help/images/understanding-morphological-reconstruction.html which is incorporated by reference herein in its entirety, as if set forth fully herein) for two thresholds, $t_1 > t_2$.

A further output of the clustering step is lesion cluster data corresponding to the output set of lesion clusters. In particular, lesion cluster data may be any data or information associated with a particular identified lesion cluster or associated with the individual lesions of a particular cluster. By way of example, the lesion cluster data may include the coordinates of each lesion in a particular lesion cluster and/or, for each lesion in that lesion cluster, one or more of the lesion properties acquired by the acquiring module 110. In particular, by way of non-limiting example, information indicative of one or more lesion properties may be stored in association with each of the plurality of lesion locations and the categorizing module 120 may be configured to retrieve information indicative of the one or more lesion properties for each of the lesion locations in an identified lesion cluster and to associate this information with that lesion cluster as lesion cluster data.

Additionally or alternatively, the lesion cluster data of a particular lesion cluster may include information about the cluster itself. That is, the lesion cluster data may include at least one lesion cluster property. By way of example, the determined lesion cluster data of each of the at least one lesion cluster may summarise a lesion cluster using its statistics such as its (multivariate) moments. For example, mean, standard deviation, variance, of spatial coordinates of each lesion location in the cluster can be used to characterise the cluster location. The covariance, (co)skewness and (co)kurtosis of spatial coordinates of each lesion location in the lesion cluster can be used to characterise the shape, spread and openness of a cluster, respectively. Calculation of statistics may be weighted by the individual lesion area or brightness.

Alternatively, a lesion cluster may be summarised by the properties of the lesions of that lesion cluster. For example a lesion cluster may be summarised by a mean, median, or mode value of a lesion property determined using the value for that property of each lesion of the lesion cluster. In this regard, a mean value may be an average or expected value of a set of values, a median value is a value separating the higher half from the lower half of the data sample such that any given value is equally likely to fall above or below the value, and a mode value of a set of values is the value that appears most often among the set.

This information may be directly output by the clustering algorithm. Alternatively, the lesion cluster data may be determined by the categorising module 120 based on the identified at least one lesion cluster output by the clustering algorithm and associated with the corresponding lesion cluster as lesion cluster data.

By way of further example, the lesion cluster data may include at least one cluster property of each of the at least one lesion cluster, the at least one cluster property comprising one or more of:

in a case where a type of lesion for each of the plurality of lesion locations in the medical image is acquired, a mode type of lesions in the lesion cluster;

in a case where a lesion area or a lesion volume for each of the plurality of lesion locations in the medical image is acquired, a mean or median lesion area or a mean or median lesion volume of lesions in the lesion cluster;

in a case where a lesion shape complexity for each of the plurality of lesion locations in the medical image is acquired, a mean or median lesion shape complexity of lesions in the lesion cluster;

in a case where a lesion intensity or a lesion colour for each of the plurality of lesion locations in the medical image is acquired, a mean or median lesion intensity or a mean or median lesion colour of lesions in the lesion cluster;

a mean location of lesions of the lesion cluster;

a median location of the lesions of the lesion cluster;

a standard deviation of locations of lesions of the lesion cluster;

a variance of locations of lesions of the lesion cluster;

a covariance value of the lesion cluster;

a skewness value of the lesion cluster;

a co-skewness value of the lesion cluster;

a kurtosis value of the lesion cluster;

a co-kurtosis value of the lesion cluster;

a lesion cluster shape complexity; and a lesion cluster area.

In process step S14 of FIG. 3, the categorizing module categorises each of the at least one lesion cluster into one of the set of predetermined categories based on the determined lesion cluster data.

The set of predetermined categories may, as in the present embodiment, be selectable by a user or operator of the apparatus 100 for one or more determinations of the level of pathology present in a medical image. Alternatively, the set of predetermined categories may be fixed. Each category may be defined in any way but it is usual that for any possible lesion cluster data there will be either no category or a unique category to which it can be assigned.

Figure 6A:
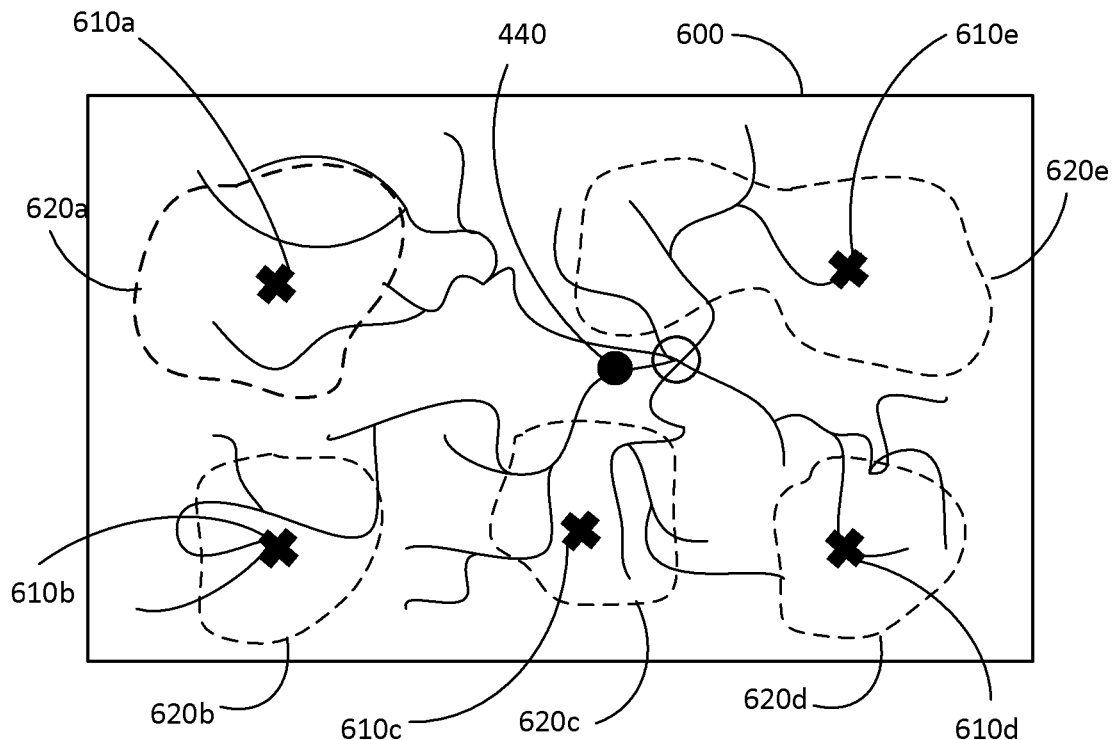
FIG. 6(a) is a schematic illustration, showing the medical image, to which clustering algorithm has been applied, in which a centroid of each of the lesion clusters is identified.
Figure 6B:
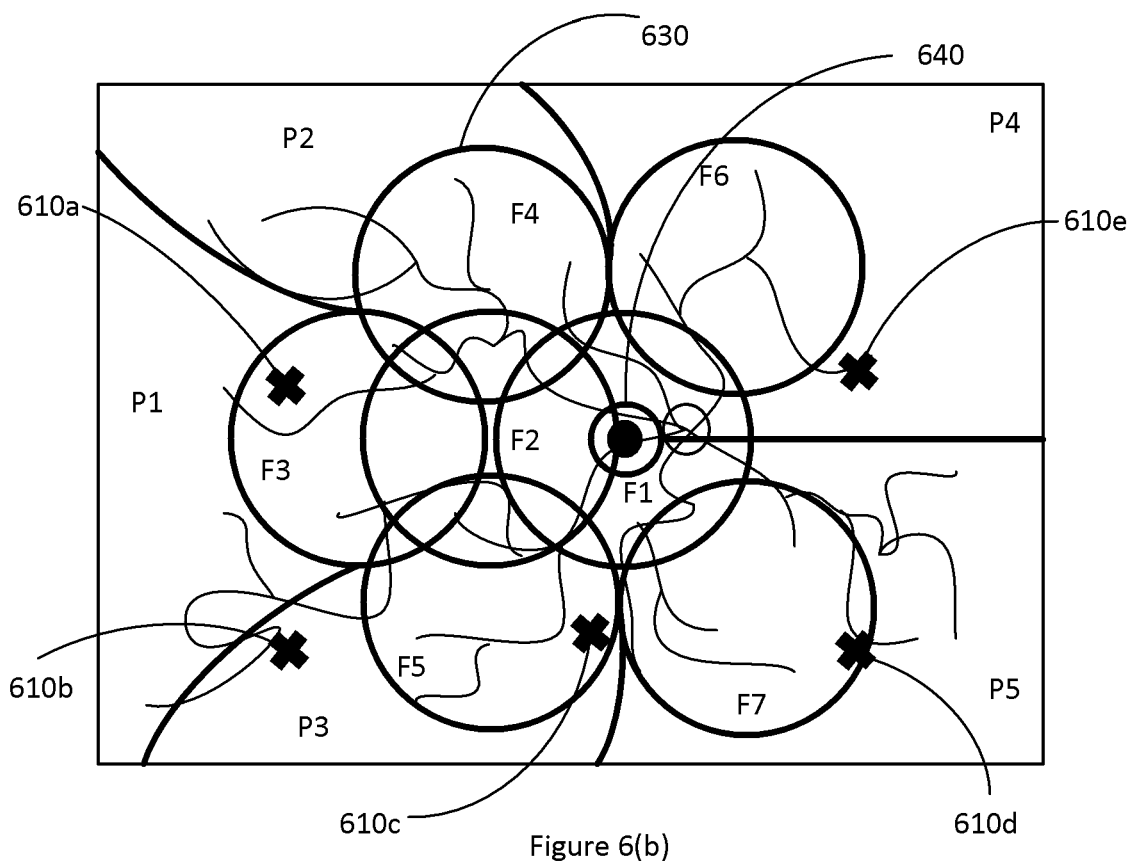
FIG. 6(b) is a schematic illustration, showing the medical image, to which clustering algorithm has been applied, in which lesion clusters are categorised according to a field in which a centroid of the cluster is located.

By way of example, the categorizing module 120 of FIG. 1 may be configured to categorise each of the at least one lesion cluster into one of a set of predetermined categories based on the determined lesion cluster data by using a grid, such as grid 630 in FIG. 6(b) to define fields (grid elements) in the medical image and categorising each of the at least one lesion cluster according to the field in which a centroid, a mean location of lesions of the at least one lesion cluster, and/or a median location of the lesions of the at least one lesion cluster is located. As shown in Fig. FIG. 6(b), the fields (grid elements) may be overlapping.

FIG. 6(a) is a schematic illustration, showing the medical image 600, to which clustering algorithm has been applied, in which a centroid 610a, 610b, 610c, 610d, 610e of each of the lesion clusters 620a, 620b, 620c, 620d, 620e, respectively, is identified. FIG. 6(b) is a schematic illustration, showing the same medical image 600, to which clustering algorithm has been applied, in which lesion clusters 620a, 620b, 620c, 620d, 620e are categorised according to a field F1, F2, F3, F4, F5, F6, F7, P1, P2, P3, P4, P5 in which a centroid 610a, 610b, 610c, 610d, 610e of the cluster is located. In the example of FIGS. 6(a) and 6(b), the medical image 600 is schematically shown as an ultra-wide field image of a portion of the retina of a subject captured using a scanning laser ophthalmoscope, SLO.

The purpose of a grid 630 is to divide the human anatomy in question (in this case a portion of the retina) into regions which allow the characterisation of location of pathology. Locating a grid 630 relative to observed anatomy is commonly used in retinal disease analysis. For example, in maculopathy grading, maculopathy may be defined using circular regions F1, F2, F3, F4, F5, F6, F7 defining the macula 640 that are centred on the fovea 440. In FIG. 6(b), the retina is divided into overlapping regions F1, F2, F3, F4, F5, F6, F7 representing standard Early Treatment Diabetic Retinopathy Study (ETDRS) fundus photography, located relative to the fovea 440 and ONH 450 (FIG. 5(b), and other regions P1, P2, P3, P4, P5 covering the remainder of the ultra-wide field retinal image.

In general, a grid, such as grid 630, comprises connected regions of an image or edges which are defined using points that have fixed coordinates (and possibly using distances such circle radii) in a coordinate system, such as any of those described above in relation to process step S10. Each field (such as, for example, fields F1, F2, F3, F4, F5, F6, F7, P1, P2, P3, P4, P5 in FIG. 6(b)) is then enclosed by a specified subset of these edges. Additionally other edges which are not defined using points that have fixed coordinates can be used. Examples of these are (a) the edges of the image or (b) the limit of visible anatomy in the image. Such edges can also be used to define the field boundaries.

As can be seen in FIG. 6(b), the centroid 610a of lesion cluster 620a is located in field F3. Similarly, the centroid 610b of lesion cluster 620b is located in field P3, the centroid 610c of lesion cluster 620c is located in field F5, the centroid 610d of lesion cluster 620d is located in field F7 and the centroid 610e of lesion cluster 620e is located in field P4. Accordingly, each of the categories corresponding to fields F3, P3, F5, F7 and P4 comprises a single lesion cluster and each of the categories corresponding to fields F1, F2, F4, F6, P1, P2, P5 does not comprise a lesion cluster (that is, the categories empty).

In the example of FIG. 6(b), each category comprises at most a single lesion cluster. However, in alternative examples, at least a subset of the categories may comprise two or more lesion clusters, depending on the number and distribution of lesion clusters identified by the categorizing module 120.

Alternatively or additionally, by way of further example, the categorizing module 120 of FIG. 1 may be configured to categorise each of the at least one lesion cluster into at least one of a set of predetermined categories based on the determined lesion cluster data by:

in a case where a type of lesion for each of the plurality of lesion locations in the medical image is acquired and the lesion cluster data of each of the at least one lesion cluster comprises a mode type of lesions in the lesion cluster, categorising each of the at least one lesion cluster according to the mode type of lesions in the lesion cluster;

in a case where, the lesion cluster data of each of the at least one lesion cluster comprises at least one of a mean, a median, a standard deviation and a variance of locations of the lesions of the lesion cluster, categorising each of the at least one lesion cluster according to the at least one of the mean, the median, the standard deviation and the variance of locations of the lesions of the lesion cluster;

in a case where, the lesion cluster data of each of the at least one lesion cluster comprises at least one of a covariance value of the lesion cluster, a skewness value of the lesion cluster, a co-skewness value of the lesion cluster, a kurtosis value of the lesion cluster and a co-kurtosis value of the lesion cluster, categorising each of the at least one lesion cluster according to a shape of the lesion cluster;

in a case where, the lesion cluster data of each of the at least one lesion cluster comprises a lesion cluster shape complexity or a lesion cluster area, categorising each of the at least one lesion cluster according to a shape complexity or area of the lesion cluster;

in a case where a lesion area or a lesion volume for each of the plurality of lesion locations in the medical image is acquired and the lesion cluster data of each of the at least one lesion cluster comprises a mean or median lesion area or a mean or median lesion volume of lesions in the lesion cluster, categorising each of the at least one lesion cluster according to the mean or median lesion area or the mean or median lesion volume of lesions in the lesion cluster;

in a case where a lesion shape complexity for each of the plurality of lesion locations in the medical image is acquired and the lesion cluster data of each of the at least one lesion cluster comprises a mean or median lesion shape complexity of lesions in the lesion cluster, categorising each of the at least one lesion cluster according to the mean or median lesion shape complexity of lesions in the lesion cluster; and in a case where a lesion colour or a lesion intensity for each of the plurality of lesion locations in the medical image is acquired and the lesion cluster data of each of the at least one lesion cluster comprises a mean or median lesion colour or a mean or median lesion intensity of lesions in the lesion cluster, categorising each of the at least one lesion cluster according to mean or median lesion colour or the mean or median lesion intensity of lesions in the lesion cluster.

Similar to the example discussed above in relation to FIG. 6(b), after the categorizing module 120 has categorised each of the at least one lesion cluster into one of the set of predetermined categories, each category of the set of predetermined categories may comprise no lesion clusters or one or more lesion clusters and their corresponding lesion cluster data.

In the example of FIG. 6(b), the number of predetermined categories is twelve. Alternatively, the number of predetermined categories may be any number greater than or equal to 2.

In process step S16 of FIG. 3, the categorizing module 120 applies at least one function to the lesion cluster data with regard to each category of the set of predetermined categories, wherein the at least one function provides a fixed number of data outputs.

The at least one function may be, for example, a statistical function, $f:S \rightarrow x$ where $S \subset \mathbb{R}$ and $x \in \mathbb{R}$ (that is, a function which takes a set of real numbers and returns a real number). Furthermore, the at least one function applied by the categorizing module 120 may be statistical function that takes an unfixed number of data as input (e.g., the number of lesions and/or number of lesion clusters in each category) and determines a known number of results (outputs) (i.e. the size of the output set associated with the statistical function of data is known prior to application of the function to the input data). For each category, one or more such functions may be used.

Each of the at least one function is applied to the lesion clusters in the category or to a property, such as a lesion cluster area, of each lesion cluster in the category. For each category the result is a data vector of known length. The results using all categories provide the fixed size data, thereby providing results that may be used as input to automated classifiers, without requiring information relating to a spatial distribution across the medical image and/or relating to the way the lesions are associated with one another to be omitted.

By way of example, at least one function may comprise at least one of:

- a count function (which may, for example, output a count of the number of clusters in a given category);
- a sum function (which may, for example, output a sum total of a numerical value, such as number of lesions in the cluster or average lesion location in the cluster, included in the lesion cluster data of each cluster in a given category);
- a mean function (which may, for example, output a mean or average value of a numerical value included in the lesion cluster data of each cluster in a given category);
- a standard deviation function (which may, for example, output a standard deviation value of a numerical value included in the lesion cluster data of each cluster in a given category);
- a skewness function (which may, for example, output a skewness value (i.e. a measure of the extent to which a distribution differs from a normal distribution) of a numerical value included in the lesion cluster data of each cluster in a given category);
- a maximum function (which may, for example, output a maximum value of a numerical value included in the lesion cluster data of each cluster in a given category); and/or
- a minimum function (which may, for example, output a minimum value of a numerical value included in the lesion cluster data of each cluster in a given category).

For example, for each category to which it is applied, the count function outputs a value indicative of the number of clusters in that category. For each category to which it is applied, each of the latter five functions may be applied to the values of particular property of each of the lesion clusters in that category.

The statistical function, and the lesion cluster data to which it is applied, may be selected towards a clinical application. That is, the selection may be designed to express a pattern of lesions distribution which is expected to have an association or correlation with a particular disease outcome. For example, in the retinal disease, AMD, the lesions are expected to be distributed around the macula. The risk to the patient may be dependent on the tendency of lesions associated with this disease to be present close to the fovea. Mean and standard deviation of distance from the fovea, would be useful statistics for quantifying the tendency of lesions to form in the macula.

By way of a further example, Table 1 below shows an example of the fixed number of outputs resulting from the categorizing module 120 applying a count function and a sum function to each of the categories corresponding to the fields F1, F2, F3, F4, F5, F6, F7, P1, P2, P3, P4, P5 of FIG. 6(b). In particular, the sum function outputs a value indicative of the sum of the values of particular property (in this case lesion cluster area) of each of the lesion clusters in a given category. In the example of FIG. 6(b), as each of the categories corresponding to fields F3, P3, F5, F7 and P4 comprises a single lesion cluster, the sum of the cluster areas of the lesion clusters in a given category is equal to the cluster area of the single lesion cluster in the category.

TABLE 1

|  | F1 | F2 | F3 | F4 | F5 | F6 | F7 | P1 | P2 | P3 | P4 | P5 |
|---|---|---|---|---|---|---|---|---|---|---|---|---|
| Count | 0 | 0 | 1 | 0 | 1 | 0 | 1 | 0 | 0 | 1 | 1 | 0 |
| Sum (Cluster Area) | 0 | 0 | $A_{620a}$ | 0 | $A_{620c}$ | 0 | $A_{620d}$ | 0 | 0 | $A_{620b}$ | $A_{620e}$ | 0 |

Accordingly, in this example, the result of the categorizing module 120 applying the at least one function to the lesion cluster data with regard to each category of the set of predetermined categories is a vector of length 24 (that is, for each of the 12 categories there are two associated values: a count value and a sum value). Here, the "0" may treated by the classifiers as an empty data field for the respective category.

Alternatively, any number or combination of functions, including those listed above, may be applied to the lesion cluster data with regard to each category of the set of predetermined categories, provided each function provides a single output or at fixed number of outputs.

In process step S18 of FIG. 3, the determining module 130 determines the pathologic condition from the medical image by processing the fixed number of outputs of each category of the set of predetermined categories using the classification algorithm trained on image data defining medical images of the portion of a plurality of subjects. That is, for each category, the output(s) of the at least one function when applied to that category are used as inputs to the classification algorithm.

By way of example, the determining module 130 may be configured to determine a level of pathology or a pathological condition that is indicative of any one or more of: the presence or absence of a pathologic condition or disease in the portion of the subject imaged; the severity of a pathologic condition or disease in the portion of the subject imaged; and the rate of advance of a pathologic condition or disease in the portion of the subject imaged.

In particular, the classification algorithm may classify the image as belonging to one of two or more pathologic levels/conditions. Where there are two levels, these levels may correspond to a determination that the portion of subject is unhealthy or healthy. Accordingly, the output of the classification algorithm may be "yes" or "no", 1 or 0, or some other binary indicator of whether or not a pathology, pathologic condition, or disease is present.

Alternatively, where the classification algorithm may classify the image as belonging to 2 or more levels, these levels may correspond to a determination of the level of severity of severity of a disease or pathology of the portion of the subject, e.g. mild, moderate, severe, etc. Alternatively, where the classification algorithm may classify the image as belonging to 2 or more levels, these levels may correspond to a determination of the rate of progress of a disease or pathology in the portion of subject, e.g. slow, moderate, fast, etc. By way of example, in a case where an earlier medical image of a portion of a subject has been previously processed to determine a level of severity of disease, a rate of progress of a disease or pathology may be determined by first determining a level of severity of the disease based on the current medical image and then determining a rate of progress based on the increase in the level of severity and the time interval between capturing the current medical image and the earlier medical image. Alternatively, the classification algorithm may be trained to identify, as part of determining a pathologic condition, any feature or characteristic of the portion of the subject being imaged that is known in the medical field to be indicative of a rate of progress of a disease.

In embodiments like the present illustrated embodiment, where the apparatus 100 comprises a display control signal generator 140, the display control signal generator 140 may be arranged to generate display control signals for controlling a display device (as shown at 215 in FIG. 2), such as an LCD screen or other type of visual display unit, to display at least a representation of the determined level of pathology. The displayed representation of the determined level of pathology may take any suitable form known in the art, for example, words, numbers, graphics, colour indicators, etc.

FIG. 7 is a schematic illustration showing how a classification algorithm may be trained on image data 701, 702 defining medical images of the portion 710 of a plurality of subjects, in accordance with a first example embodiment herein. In the example of FIG. 7, the images defined by image data 701, 702 are images of a portion of the retina of a plurality of subjects captured using a scanning laser ophthalmoscope, SLO, 350 but may be any form of medical image in which lesions may be present (such as, for example, a medical image of a subject's brain, lungs and skin), depending on the portion of the subject for which a level of pathology is to be determined.

In particular, image data 702 defines images of healthy eyes, and image data 701 defines images of unhealthy eyes. In this context, a healthy eye is one in which lesions are not present and an unhealthy eye is one in which lesions, caused by a particular disease or pathology, are present. The identification that a particular disease or pathology is present (rather than merely identifying that lesions are present) may depend on the spatial distribution of lesions and lesion clusters. Therefore, a healthy eye may also be one in which lesions are present, but not in a form indicative of the particular disease or pathology in question. A learning algorithm 730 is configured to learn from, and make predictions based on, input data by building a model 740 (classification algorithm) from an example training set 700 of input data, comprising the image data 702 defining images of the retina of healthy eyes, and the image data 701 defining images of the retina of unhealthy eyes. By way of example, image data 701 defines images of the portion of unhealthy eyes, each of which has a plurality of lesions. The images defined by the image data 701 in the example training set 700 may be collected by acquiring images of the retinas of multiple subjects. More generally, each image is of the same portion (in this case, the retina of the eye 710) of a subject or of substantially the same portion of a subject or of a part of a subject containing the same portion as the portion of the subject for which a level of pathology is to be determined. Furthermore, each image defined by the image data in the example training set 700 is acquired by the medical imaging system 350 or by a same type of medical imaging system and operating in a same imaging modality.

The learning algorithm may, as in the present embodiment, be a supervised learning algorithm. In particular, the learning algorithm may, as in the present embodiment, be a supervised learning algorithm comprising a neural network.

In embodiments where the learning algorithm 730 is a supervised learning algorithm (such as a neural network, a support vector machine or an evolutionary algorithm, for example), each example image in the example training set 700 is a pair consisting of input image data defining an image of the portion of a subject and a desired output value indicating whether the image is of a portion of a "healthy" or "unhealthy" portion (in this case, the retina of the eye). The supervised learning algorithm 730 analyses the image data in the example training set 700 and produces a model or classification algorithm 740, which can be used to classify new unseen image data defining an image of the portion of a subject as "healthy" or "unhealthy".

In one example embodiment herein, as the learning algorithm 730 is trained on an example training set 700 in which image data 701, 702 is classified as "healthy" or "unhealthy" only, the model 740 cannot distinguish between levels of severity of pathology in the portion of subject imaged or rates of advance of pathology in the portion subject imaged. It can only determine whether a pathology, for example, severe diabetic retinopathy, is present or not.

Figure 8:
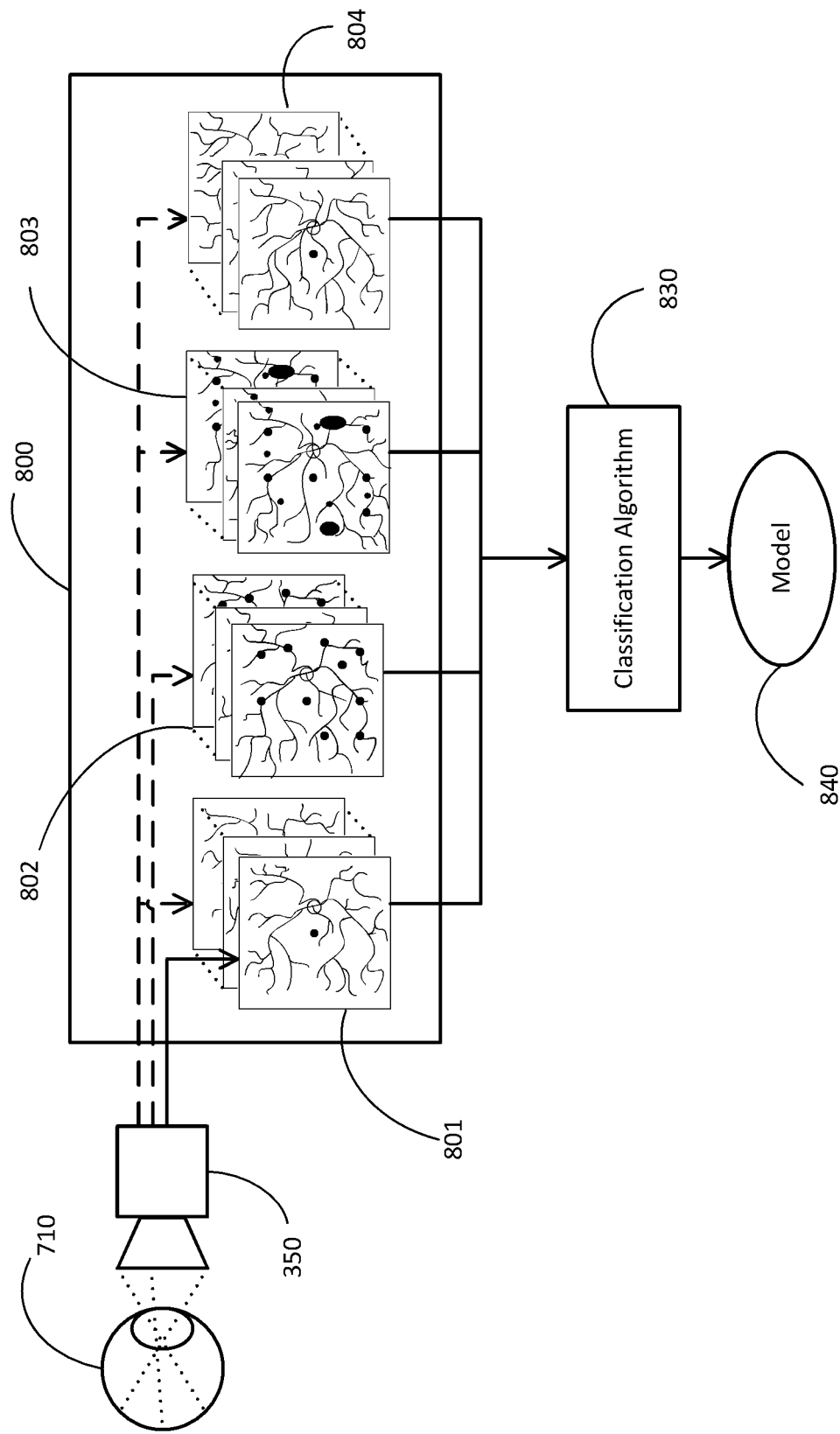
FIG. 8 is a schematic illustration showing how the classification algorithm may be trained on image data defining medical images of the portion of a plurality of subjects, in accordance with a second example embodiment herein.

FIG. 8 is a schematic illustration showing how the learning algorithm 830 may be trained on image data 801, 802, 803, 804 defining medical images of the portion of a plurality of subjects, in accordance with a second example embodiment herein. Similar to FIG. 7, in the example of FIG. 8, the images defined by image data 801, 802, 803, 804 are images of a portion of the retina of a plurality of subjects captured using a scanning laser ophthalmoscope, SLO, 350 but may be any form of medical image in which lesions may be present (such as, for example, a medical image of a subject's brain, lungs and skin), depending on the portion of the subject for which a level of pathology is to be determined.

By way of example, image data 801 defines images of the portion of unhealthy eyes which have moderate non-peripheral diabetic retinopathy, image data 802 defines images of the portion of unhealthy eyes which have severe non-peripheral diabetic retinopathy, and image data 803 defines images of the portion of unhealthy eyes which have peripheral diabetic retinopathy. Image data 804 defines images of the portion of healthy eyes which do not have diabetic retinopathy (and may or may not have other diseases or pathologies).

A learning algorithm 830 is configured to learn from, and make predictions based on, input data by building a model or classification algorithm 840 from an example training set 800 of input data, comprising the image data 804 defining images of the retina of healthy eyes, and the image data 801, 802, 803 defining images of the retina of unhealthy eyes. The images defined by the image data 801 to 804 in the example training set 800 may be collected by acquiring images of the retinas of multiple subjects. More generally, each image is of the same portion (in this case, the retina of the eye 710) of a subject or of substantially the same portion of a subject or of a part of a subject containing the same portion as the portion of the subject for which a level of pathology is to be determined. Furthermore, each image defined by the image data in the example training set 800 is acquired by the medical imaging system 350 or by a same type of medical imaging system and operating in a same imaging modality.

The learning algorithm 830 may be a supervised learning algorithm. Thus, each example image of the portion of the eye 710 in the example training set 800 is associated with an indicator indicating whether that image is of a portion of a "healthy" or an "unhealthy" eye and, in cases where the image is of a portion of a "unhealthy" eye, also a second indicator indicating a determined level of severity of the pathology (in this case, diabetic retinopathy) and the portion of subject imaged. The supervised learning algorithm analyses the image data in the example training set 800 and produces a model 840 (classification algorithm), which can be used to classify new (previously unseen) image data defining an image of the portion of the subject as one of, for example: "healthy"; "unhealthy—moderate non-proliferative diabetic retinopathy"; "unhealthy—severe non-proliferative diabetic retinopathy"; and "unhealthy—proliferative diabetic retinopathy".

In will be evident to one skilled in the art that the apparatus 100 may be adapted to classify additional levels of severity of pathology by expanding the training set 800 to include, for each of the additional levels of severity of pathology, image data defining images of the retina (or other portion) of the subject having that level of severity, and associated indicators as described above. For example, the training set 800 may be expanded to include image data defining images of the portion of unhealthy eyes having mild non-proliferative diabetic retinopathy. Furthermore, any of the image data 801, 802, 803 defining images of the portion of unhealthy eyes may be removed or replaced with image data defining images of the portion of unhealthy eyes having a different level of severity of pathology. A revised version of the model or classification algorithm 840 may then be produced based on the modified training set 800. By way of further alternative, the image data 801, 802, 803 defining images of the portion of unhealthy eyes may be removed and replaced with image data defining images of the portion of unhealthy eyes having different levels of rate of advance of pathology. A revised version of the model or classification algorithm 840 may then be produced based on the modified training set 800.

The supervised learning algorithm 830 may, as in the present example embodiment, be a neural network, such as for example a convolutional neural network. Convolutional neural networks are particularly suitable to image and video recognition tasks. Neural networks automatically generate identifying characteristics by processing the input data, such as the image data in the example training set 800, without any prior knowledge.

Figure 9:
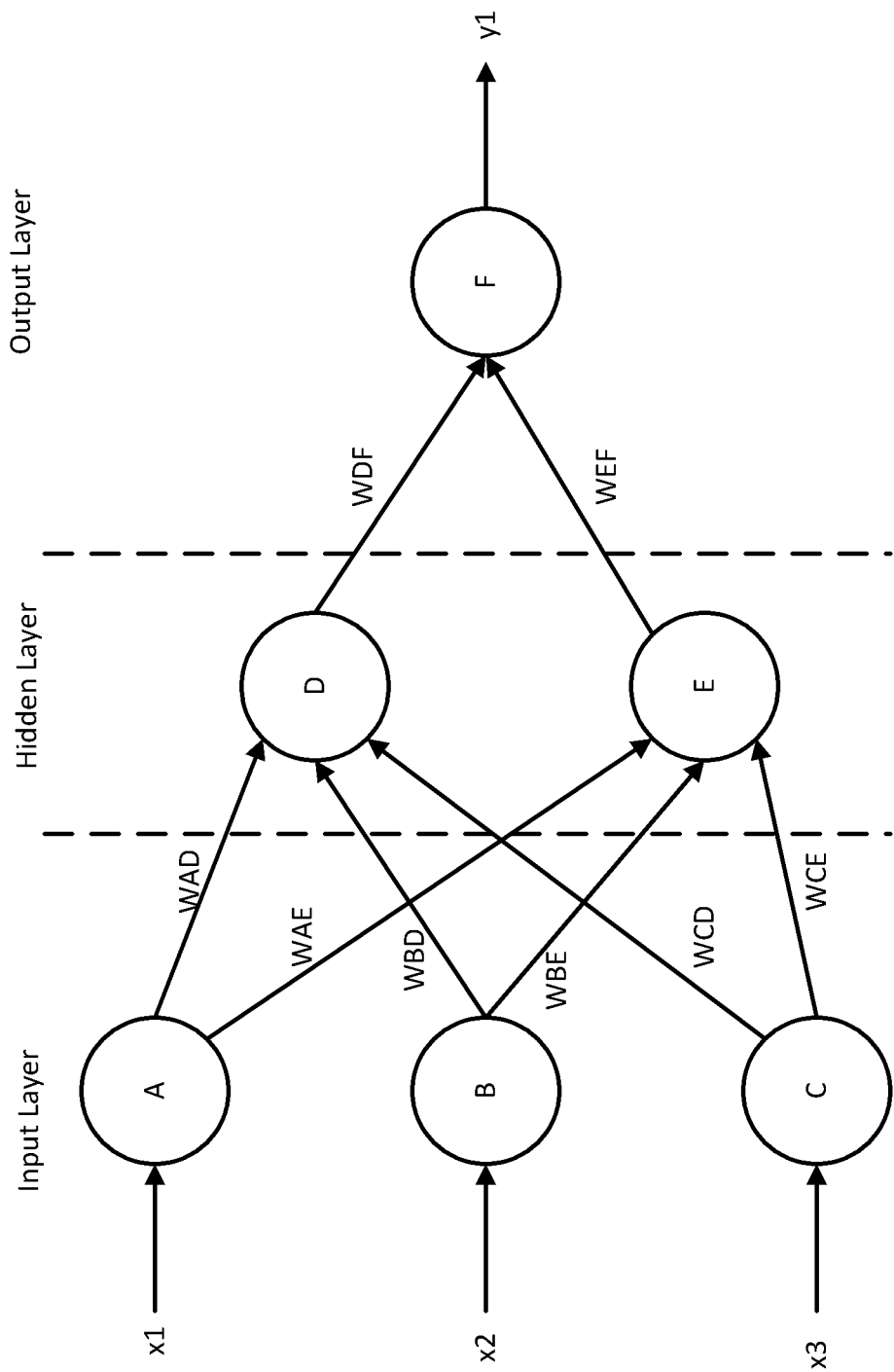
FIG. 9 is a schematic illustration of a neural network comprising artificial neurons and an input layer, a hidden layer, and an output layer.

As illustrated in FIG. 9, in general, a neural network consists of an input layer (having example inputs $x1$, $x2$, and $x3$ as shown, although more or less inputs also can be provided) and an output layer, as well as multiple hidden layers. Each of the layers is composed of a plurality of artificial neurons (labelled A to F in FIG. 9), and each layer may perform different kinds of transformations on their inputs. Each artificial neuron may be connected to multiple artificial neurons in adjacent layers. The output of each artificial neuron is computed by some non-linear function of the sum of its inputs. Artificial neurons and the connections therebetween typically have respective weights (WAD, WAE, etc. in FIG. 9) which determine the strength of the signal at a given connection. These weights are adjusted as learning proceeds, thereby adjusting the output of the neural network. Signals travel from the first layer (the input layer), to the last layer (the output layer), and may traverse the layers multiple times.

The output ($y1$) of the neural network may be viewed as a probability of the input medical image data containing identifying characteristics of a particular level of pathology (for example, any of those discussed above) and the classification may, as in the present example embodiment, comprise determining whether the output of the trained model 840 exceeds a predetermined threshold. The predetermined threshold may represent an acceptably low probability that the input image data contains identifying characteristics of a particular level of pathology and, therefore, a high probability that the eye of the subject is healthy.

Figure 10:
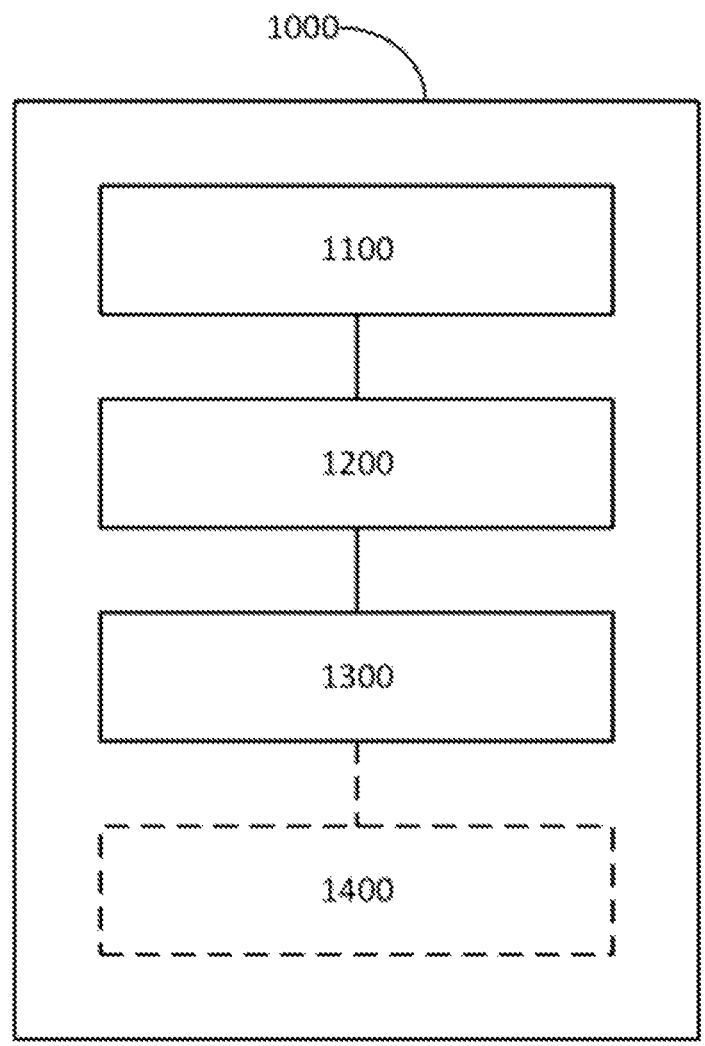
FIG. 10 is a schematic illustration of an apparatus for determining a pathologic condition from a medical image of a portion of a subject captured using a medical imaging system, according to an example embodiment herein.

Details of a further example embodiment herein will be set out below in relation to FIG. 10 and FIG. 11. FIG. 10 is a schematic illustration of an apparatus 1000 for processing medical image data of a portion of the subject captured using a medical imaging system to determine the level of pathology present in a medical image defined by the medical image data, according to an example embodiment herein. The apparatus 1000 of this example embodiment comprises components 1100, 1200, 1300, and 1400 that are the same as components 110, 120, 130, 140, respectively, of the apparatus 100 of FIG. 1, but the apparatus 1000 differs in function from the apparatus 100 of FIG. 1 in that the apparatus 1000 of FIG. 10 is not required to apply a clustering algorithm to the plurality of lesion locations in the medical image. The apparatus 1000 of FIG. 10 may be implemented by a signal processing hardware configuration, such as that shown in the FIG. 2, or by any other suitable means.

The apparatus 1000 of FIG. 10 comprises an acquiring module 1100, a categorizing module 1200, and a determining module 1300. As discussed above in relation to apparatus 100 of FIG. 1, the apparatus 1000 may, optionally, further comprise a display control signal generator 1400. The functional and structural features of each of these elements (and any alternatives) are as described above in relation to corresponding elements of the apparatus 100 of FIG. 1 above, unless specifically stated otherwise.

Figure 11:
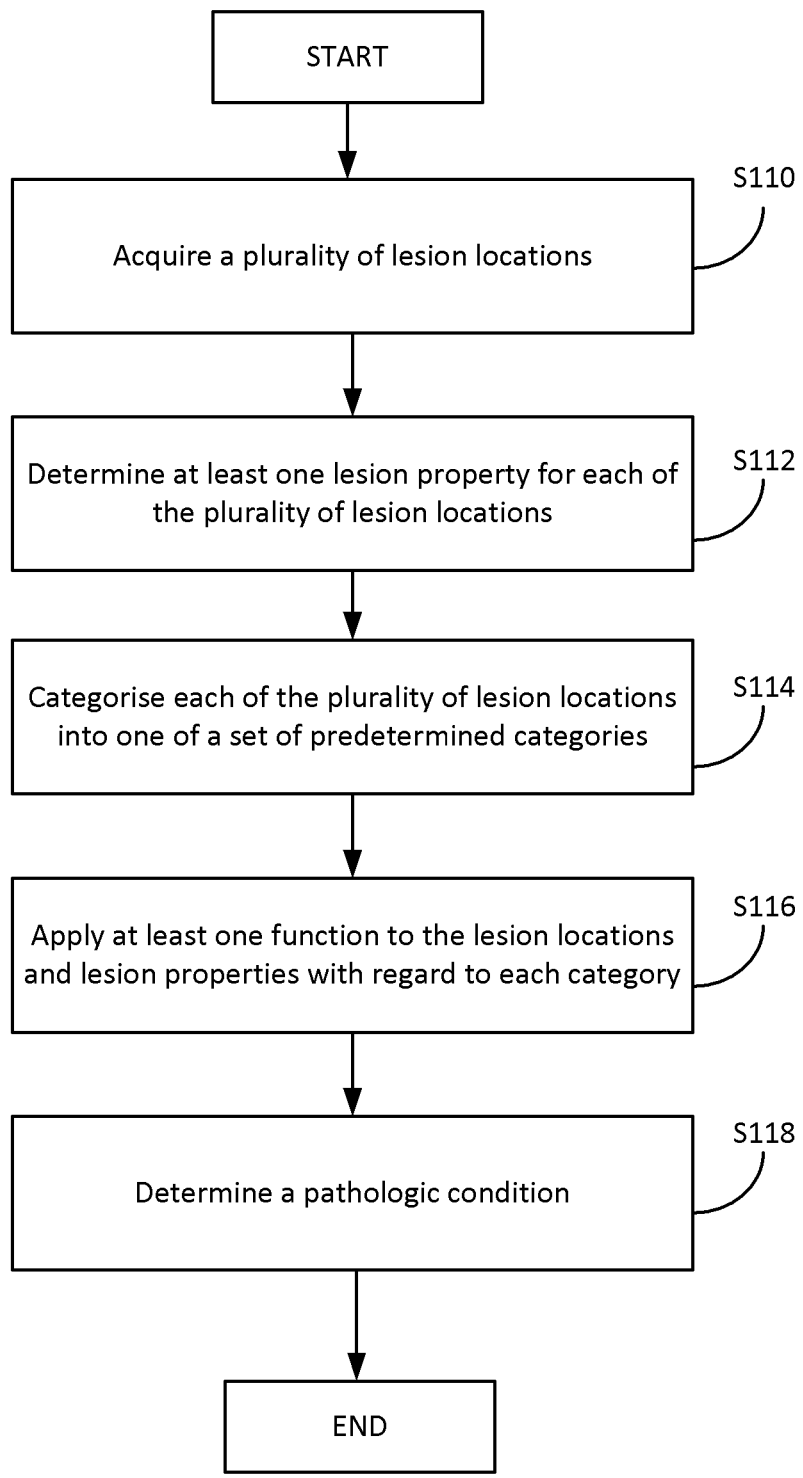
FIG. 11 is a flow diagram illustrating a process by an apparatus FIG. 10 processes medical image data to determine a pathologic condition, in accordance with an example embodiment herein.

FIG. 11 is a flow diagram illustrating a process by an apparatus 1000 of FIG. 10 processes medical image data to determine the level of pathology, in accordance with an example embodiment herein.

In process step S110 of FIG. 11, the acquiring module 1100 acquires a plurality of lesion locations in the medical image. The acquiring module 1100 may, optionally, be configured to acquire a plurality of lesion locations in the medical image by any of the means discussed above in relation to the apparatus 100 of FIG. 1, for example by an automated lesion detector 300 (and/or medical imaging system 350).

In process step S112 of FIG. 11, the categorising module 1200 determines at least one lesion property for each of the plurality of lesion locations in the medical image. Alternatively, the lesion property may be determined by an automated lesion detector 300.

The categorising module 1200 may, optionally, be configured to determine the at least one lesion property for each of the plurality of lesion locations by any of the means discussed above in relation apparatus 100 of FIG. 1. Furthermore, the at least one lesion property may be any of those discussed above in relation to apparatus 100 of FIG. 1.

In process step S114 of FIG. 11, the categorising module 1200 categorises each of the plurality of lesion locations into one of a set of predetermined categories based on the determined lesion property.

By way of non-limiting example, categorising each of the plurality of lesion locations into one of a set of predetermined categories based on the determined lesion property may comprise any one or more of:

using a grid to define fields in the medical image and categorising each of the plurality of lesion locations according to the field in which the lesion is located;

in a case where a type of lesion for each of the plurality of lesion locations in the medical image is acquired as the lesion property, categorising each of the plurality of lesion locations according to the type of lesion;

in a case where a lesion area or a lesion volume for each of the plurality of lesion locations in the medical image is acquired as the lesion property, categorising each of the plurality of lesion locations according to the lesion area or the lesion volume;

in a case where a lesion shape complexity for each of the plurality of lesion locations in the medical image is acquired as the lesion property, categorising each of the plurality of lesion locations according to the lesion shape complexity; and in a case where a lesion colour or a lesion intensity for each of the plurality of lesion locations in the medical image is acquired as lesion property, categorising each of the plurality of lesion locations according to lesion colour or the lesion intensity.

In process step S116 of FIG. 11, the categorising module 1200 applies at least one function to the lesion locations and lesion properties with regard to each category of the set of predetermined categories, wherein the at least one function provides a fixed number of data outputs.

The at least one function applied by the categorising module 1200 may, optionally, be any of those discussed above in relation to apparatus 100 of FIG. 1. However, in this embodiment, the at least one function is applied directly to the lesion locations and/or the values of a lesion property of each of the lesion locations in a particular category, rather than to lesion cluster data.

In process step S118 of FIG. 11, the determining module 1300 determines a pathologic condition from the medical image by processing the fixed number of data outputs of each category of the set of predetermined categories based on a classification algorithm trained on image data defining medical images of the portion of a plurality of subjects.

The pathologic condition determined may, optionally, be any of those discussed above in relation to apparatus 100 of FIG. 1. The classification algorithm may be any of those discussed above in relation to the apparatus 100 of FIG. 1.

At least some of the embodiments described above are summarised in the following examples E1 to E16.

E1. An apparatus (100) for determining a pathologic condition from a medical image of a portion of a subject captured using a medical imaging system, the apparatus (100) comprising: an acquiring module (110) configured to acquire a plurality of lesion locations in the medical image; a categorizing module (120) configured to: apply a clustering algorithm to the plurality of lesion locations in order to identify at least one lesion cluster and corresponding lesion cluster data; categorize each of the at least one lesion cluster into one of a set of predetermined categories based on the lesion cluster data; and apply at least one function to the lesion cluster data with regard to each category of the set of predetermined categories, wherein the at least one function provides a fixed number of data outputs; and a determining module (130) configured to determine a pathologic condition from the image by processing the fixed number of data outputs of each category of the set of predetermined categories based on a classification algorithm trained on image data defining medical images of the portion of a plurality of subjects.

E2. The apparatus (100) of E1, wherein the acquiring module (110) is further configured to acquire, as a lesion property, at least one of a type of lesion, a lesion area, a lesion volume, lesion shape complexity, a lesion intensity, and a lesion colour for each of the plurality of lesion locations in the medical image.

E3. The apparatus (100) of E2, wherein the categorizing module (120) is further configured to apply the clustering algorithm with regard to the plurality of lesion locations having a same lesion property.

E4. The apparatus (100) of any of E1-E3, wherein each location of the plurality of lesion locations is defined in a two-dimensional image-based coordinate system or in a coordinate system adapted to the portion of the subject being imaged.

E5. The apparatus (100) of any of E1-E4, wherein the clustering algorithm does not require, as input, an indication of a number of clusters.

E6. The apparatus (100) of any of E1-E5, wherein the clustering algorithm comprises at least one of: a density-based spatial clustering of applications with noise, DBSCAN, algorithm; or applying a threshold to a bandpass filtered map of the plurality of lesion locations.

E7. The apparatus (100) of any of E1-E6, wherein the lesion cluster data include at least one cluster property of each of the at least one lesion cluster, the at least one cluster property comprising one or more of: in a case where a type of lesion for each of the plurality of lesion locations in the medical image is acquired, a mode type of lesions in the lesion cluster; in a case where a lesion area or a lesion volume for each of the plurality of lesion locations in the medical image is acquired, a mean or median lesion area or a mean or median lesion volume of lesions in the lesion cluster; in a case where a lesion shape complexity for each of the plurality of lesion locations in the medical image is acquired, a mean or median lesion shape complexity of lesions in the lesion cluster; in a case where a lesion intensity or a lesion colour for each of the plurality of lesion locations in the medical image is acquired, a mean or median lesion intensity or a mean or median lesion colour of lesions in the lesion cluster; a mean location of lesions of the lesion cluster; a median location of the lesions of the lesion cluster; a standard deviation of locations of lesions of the lesion cluster; a variance of locations of lesions of the lesion cluster; a covariance value of the lesion cluster; a skewness value of the lesion cluster; a co-skewness value of the lesion cluster; a kurtosis value of the lesion cluster; a co-kurtosis value of the lesion cluster; a lesion cluster shape complexity; and a lesion cluster area.

E8. The apparatus (100) of any of E1-E7, wherein the categorizing module (120) is further configured to categorize each of the at least one lesion cluster into one of a set of predetermined categories based on the lesion cluster data by any one or more of: using a grid to define fields in the medical image and categorising each of the at least one lesion cluster according to the field in which a centroid, a mean location of lesions of the at least one lesion cluster or a median location of the lesions of the at least one lesion cluster is located; in a case where a type of lesion for each of the plurality of lesion locations in the medical image is acquired and the lesion cluster data of each of the at least one lesion cluster comprises a mode type of lesions in the lesion cluster, categorising each of the at least one lesion cluster according to the mode type of lesions in the lesion cluster; in a case where, the lesion cluster data of each of the at least one lesion cluster comprises at least one of a mean, a median, a standard deviation and a variance of locations of the lesions of the lesion cluster, categorising each of the at least one lesion cluster according to the at least one of the mean, the median, the standard deviation and the variance of locations of the lesions of the lesion cluster; in a case where the lesion cluster data of each of the at least one lesion cluster comprises at least one of a covariance value of the lesion cluster, a skewness value of the lesion cluster, a kurtosis value of the lesion cluster and a co-kurtosis value of the lesion cluster, categorising each of the at least one lesion cluster according to a shape of the lesion cluster; in a case where the at cluster data of each of the at least one lesion cluster comprises a lesion cluster shape complexity or a lesion cluster area, categorising each of the at least one lesion cluster according to a shape complexity or area of the lesion cluster; in a case where a lesion area or a lesion volume for each of the plurality of lesion locations in the medical image is acquired and the lesion cluster data of each of the at least one lesion cluster comprises a mean or median lesion area or a mean or median lesion volume of lesions in the lesion cluster, categorising each of the at least one lesion cluster according to the mean or median lesion area or the mean or median lesion volume of lesions in the lesion cluster; in a case where a lesion shape complexity for each of the plurality of lesion locations in the medical image is acquired and the lesion cluster data of each of the at least one lesion cluster comprises a mean or median lesion shape complexity of lesions in the lesion cluster, categorising each of the at least one lesion cluster according to the mean or median lesion shape complexity of lesions in the lesion cluster; and in a case where a lesion colour or a lesion intensity for each of the plurality of lesion locations in the medical image is acquired and the lesion cluster data of each of the at least one lesion cluster comprises a mean or median lesion colour or a mean or median lesion intensity of lesions in the lesion cluster, categorising each of the at least one lesion cluster according to mean or median lesion colour or the mean or median lesion intensity of lesions in the lesion cluster.

E9. The apparatus (100) of any of E1-E8, wherein the at least one function comprises at least one of: a count function; a sum function; a mean function; a standard deviation function; a maximum function; and a minimum function.

E10. The apparatus (100) of any of E1-E9, wherein the classification algorithm is a supervised learning algorithm.

E11. The apparatus (100) of any of E1-E9, wherein the determined pathologic condition is indicative of any one or more of: a presence or absence of a disease in the portion of the subject imaged; a severity of a disease in the portion of the subject imaged; and a rate of advance of a disease in the portion of the subject imaged.

E12. The apparatus (100) of any of E1-E11, wherein the medical image is any one of: an ocular image captured using an ocular imaging system; an image of lungs captured using an x-ray imaging system, a computed tomography (CT) imaging system, or a low dose CT (LDCT) imaging system; an image of a brain captured using a magnetic resonance imaging (MRI) imaging system; and an image of skin captured using a camera.

E13. The apparatus (100) of any of E1-E12, wherein the acquiring module (110) is further configured to acquire a location of at least one lesion in the medical image by receiving medical image data of the medical image; and processing the medical image data in order to determine the location of each of a plurality of lesions in the medical image E14. A computer program which, when executed by a computer, causes the computer to perform a method comprising: acquiring (S10) a plurality of lesion locations in the medical image; applying (S12) a clustering algorithm to the plurality of lesion locations in order to identify at least one lesion cluster and corresponding lesion cluster data; categorizing (S14) each of the at least one lesion cluster into one of a set of predetermined categories based on the identified lesion cluster data; applying (S16) at least one function to the lesion cluster data with regard to each category of the set of predetermined categories, wherein the at least one function provides a fixed number of data outputs; and determining (S18) a pathologic condition from the medical image by processing the fixed number of data outputs of each category of the set of predetermined categories based on a classification algorithm trained on image data defining medical images of the portion of a plurality of subjects.

E15. A non-transitory computer-readable storage medium storing the computer program according to E14.

E16. A signal carrying the computer program according to E15.

The example aspects described herein avoid limitations, specifically rooted in computer technology, relating to conventional computerized and automated classifiers, such as an artificial neural network, a linear model, a support vector machine or a K-nearest neighbour classifier, which require fixed data arrays as inputs. By virtue of the example aspects described herein, for example, training of an automated classifier (such as, e.g., based on one or more machine-learning algorithms) for predicting/detecting a disease state or pathological condition based on lesion statistics, can be performed even in the case of a variable (not fixed) number of data, and/or in the case of a fixed number of data as well and even in a case where the automated classifier requires a fixed input data array. Furthermore, the example aspects herein allow a summary of a variable number of data to be provided while minimising the undesirable omission of useful information as to, e.g., a spatial distribution of lesions. By virtue of the capabilities of the example aspects described herein, which are rooted in computer technology, the example aspects described herein improve computer processing (e.g., by being able to handle either or both of fixed and non-fixed data arrays as inputs), and also improve the field(s) of medical imaging and medical devices, in addition to improving clinical protocols based on parameters of lesion distribution in the human body and obtaining improved facilitation of determinations of pathological levels or conditions indicated in medical images.

In the foregoing description, example aspects are described with reference to several example embodiments. Accordingly, the specification should be regarded as illustrative, rather than restrictive. Similarly, the figures illustrated in the drawings, which highlight the functionality and advantages of the example embodiments, are presented for example purposes only. The architecture of the example embodiments is sufficiently flexible and configurable, such that it may be utilized (and navigated) in ways other than those shown in the accompanying figures.

Software embodiments of the examples presented herein may be provided as, a computer program, or software, such as one or more programs having instructions or sequences of instructions, included or stored in an article of manufacture such as a machine-accessible or machine-readable medium, an instruction store, or computer-readable storage device, each of which can be non-transitory, in one example embodiment. The program or instructions on the non-transitory machine-accessible medium, machine-readable medium, instruction store, or computer-readable storage device, may be used to program a computer system or other electronic device. The machine- or computer-readable medium, instruction store, and storage device may include, but are not limited to, floppy diskettes, optical disks, and magneto-optical disks or other types of media/machine-readable medium/instruction store/storage device suitable for storing or transmitting electronic instructions. The techniques described herein are not limited to any particular software configuration. They may find applicability in any computing or processing environment. The terms "computer-readable", "machine-accessible medium", "machine-readable medium", "instruction store", and "computer-readable storage device" used herein shall include any medium that is capable of storing, encoding, or transmitting instructions or a sequence of instructions for execution by the machine, computer, or computer processor and that causes the machine/computer/computer processor to perform any one of the methods described herein. Furthermore, it is common in the art to speak of software, in one form or another (e.g., program, procedure, process, application, module, unit, logic, and so on), as taking an action or causing a result. Such expressions are merely a shorthand way of stating that the execution of the software by a processing system causes the processor to perform an action to produce a result.

Some embodiments may also be implemented by the preparation of application-specific integrated circuits, field-programmable gate arrays, or by interconnecting an appropriate network of conventional component circuits.

Some embodiments include a computer program product. The computer program product may be a storage medium or media, instruction store(s), or storage device(s), having instructions stored thereon or therein which can be used to control, or cause, a computer or computer processor to perform any of the procedures of the example embodiments described herein. The storage medium/instruction store/storage device may include, by example and without limitation, an optical disc, a ROM, a RAM, an EPROM, an EEPROM, a DRAM, a VRAM, a flash memory, a flash card, a magnetic card, an optical card, nanosystems, a molecular memory integrated circuit, a RAID, remote data storage/archive/warehousing, and/or any other type of device suitable for storing instructions and/or data.

Stored on any one of the computer-readable medium or media, instruction store(s), or storage device(s), some implementations include software for controlling both the hardware of the system and for enabling the system or microprocessor to interact with a human user or other mechanism utilizing the results of the example embodiments described herein. Such software may include without limitation device drivers, operating systems, and user applications. Ultimately, such computer-readable media or storage device(s) further include software for performing example aspects of the invention, as described above.

Included in the programming and/or software of the system are software modules for implementing the procedures described herein. In some example embodiments herein, a module includes software, although in other example embodiments herein, a module includes hardware, or a combination of hardware and software.

While various example embodiments of the present invention have been described above, it should be understood that they have been presented by way of example, and not limitation. It will be apparent to persons skilled in the relevant art(s) that various changes in form and detail can be made therein. Thus, the present invention should not be limited by any of the above described example embodiments, but should be defined only in accordance with the following claims and their equivalents.

Further, the purpose of the Abstract is to enable the Patent Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the example embodiments presented herein in any way. It is also to be understood that the procedures recited in the claims need not be performed in the order presented.

While this specification contains many specific embodiment details, these should not be construed as limitations on the scope of any inventions or of what may be claimed, but rather as descriptions of features specific to particular embodiments described herein. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

In certain circumstances, multitasking and parallel processing may be advantageous. Moreover, the separation of various components in the embodiments described above should not be understood as requiring such separation in all embodiments, and it should be understood that the described program components and systems can generally be integrated together in a single software product or packaged into multiple software products.

Having now described some illustrative embodiments and embodiments, it is apparent that the foregoing is illustrative and not limiting, having been presented by way of example. In particular, although many of the examples presented herein involve specific combinations of apparatus or software elements, those elements may be combined in other ways to accomplish the same objectives. Acts, elements and features discussed only in connection with one embodiment are not intended to be excluded from a similar role in other embodiments or embodiments.

The apparatus and computer programs described herein may be embodied in other specific forms without departing from the characteristics thereof. The foregoing embodiments are illustrative rather than limiting of the described systems and methods. Scope of the apparatus and computer programs described herein is thus indicated by the appended claims, rather than the foregoing description, and changes that come within the meaning and range of equivalency of the claims are embraced therein.

The invention claimed is:

1. A non-transitory computer-readable storage medium storing computer program instructions that, when executed by a computer, cause the computer to execute a method of determining a pathologic condition that presents as lesions on a portion of a subject from a medical image of the portion of the subject in which the lesions are visible, the image having been captured using a medical imaging system, the method comprising:
    acquiring a plurality of lesion locations in the medical image from an automated lesion detector that identified the plurality of lesion locations in the medical image;
    applying a clustering algorithm to the plurality of lesion locations to identify at least one lesion cluster and corresponding lesion cluster data;
    categorizing each lesion cluster of the at least one lesion cluster into a category of a set of predetermined categories based on the corresponding lesion cluster data, thereby generating a set of categories from the set of predetermined categories that each comprises one or more lesion clusters of the at least one lesion cluster;
    applying, for each category of the generated set of categories, at least one function to the corresponding lesion cluster data for the one or more lesion clusters of the category to generate a predetermined quantity of data outputs for the category; and
    determining a pathologic condition from the medical image by using a classification algorithm to process the predetermined quantity of data outputs of each category of the set of categories, wherein the classification algorithm processes a number of inputs that corresponds to the predetermined quantity of data outputs and is trained based on image data defining medical images of the portion of a plurality of subjects using one or more machine learning algorithms,
    wherein a function of the at least one function is a statistical function, which takes a set of real numbers and returns a real number.

2. The non-transitory computer-readable storage medium of claim 1, the method further comprising:
    acquiring, as a lesion property, at least one of a type of lesion, a lesion area, a lesion volume, lesion shape complexity, a lesion intensity, and a lesion colour for each of the plurality of lesion locations in the medical image.

3. The non-transitory computer-readable storage medium of claim 2, the method further comprising:
    applying the clustering algorithm with regard to the plurality of lesion locations having a same lesion property.

4. The non-transitory computer-readable storage medium of claim 2, the method further comprising:
    applying the clustering algorithm to lesion property data.

5. The non-transitory computer-readable storage medium of claim 1, wherein each location of the plurality of lesion locations is defined in a two-dimensional image-based coordinate system or in a coordinate system adapted to the portion of the subject being imaged.

6. The non-transitory computer-readable storage medium of claim 1, wherein the clustering algorithm does not require, as input, an indication of a quantity of clusters.

7. The non-transitory computer-readable storage medium of claim 1, wherein the clustering algorithm comprises at least one of:
    a Density-based Spatial Clustering of Applications with Noise, DBSCAN, algorithm; or
    applying a threshold to a bandpass filtered map of the plurality of lesion locations.

8. The non-transitory computer-readable storage medium of claim 1, wherein the lesion cluster data include at least one cluster property of each of the at least one lesion cluster, the at least one cluster property comprising one or more of:
    in a case where a type of lesion for each of the plurality of lesion locations in the medical image is acquired, a mode type of lesions in the lesion cluster;
    in a case where a lesion area or a lesion volume for each of the plurality of lesion locations in the medical image is acquired, a mean or median lesion area or a mean or median lesion volume of lesions in the lesion cluster;
    in a case where a lesion shape complexity for each of the plurality of lesion locations in the medical image is acquired, a mean or median lesion shape complexity of lesions in the lesion cluster;
    in a case where a lesion intensity or a lesion colour for each of the plurality of lesion locations in the medical image is acquired, a mean or median lesion intensity or a mean or median lesion colour of lesions in the lesion cluster;
    a mean location of lesions of the lesion cluster;
    a median location of the lesions of the lesion cluster;
    a standard deviation of locations of lesions of the lesion cluster; a variance of locations of lesions of the lesion cluster;
    a covariance value of the lesion cluster;
    a skewness value of the lesion cluster;
    a co-skewness value of the lesion cluster;
    a kurtosis value of the lesion cluster;
    a co-kurtosis value of the lesion cluster;
    a lesion cluster shape complexity; and
    a lesion cluster area.

9. The non-transitory computer-readable storage medium of claim 1, wherein categorizing each of the at least one lesion cluster into one of a set of predetermined categories based on the lesion cluster data comprises any one or more of:
- using a grid to define fields in the medical image and categorizing each of the at least one lesion cluster according to the field in which a centroid, a mean location of lesions of the at least one lesion cluster or a median location of the lesions of the at least one lesion cluster is located;
- in a case where a type of lesion for each of the plurality of lesion locations in the medical image is acquired and the lesion cluster data of each of the at least one lesion cluster comprises a mode type of lesions in the lesion cluster, categorizing each of the at least one lesion cluster according to the mode type of lesions in the lesion cluster;
- in a case where, the lesion cluster data of each of the at least one lesion cluster comprises at least one of a mean, a median, a standard deviation and a variance of locations of the lesions of the lesion cluster, categorizing each of the at least one lesion cluster according to the at least one of the mean, the median, the standard deviation and the variance of locations of the lesions of the lesion cluster;
- in a case where the lesion cluster data of each of the at least one lesion cluster comprises at least one of a covariance value of the lesion cluster, a skewness value of the lesion cluster, a co-skewness value of the lesion cluster, a kurtosis value of the lesion cluster and a co-kurtosis value of the lesion cluster, categorizing each of the at least one lesion cluster according to a shape of the lesion cluster;
- in a case where the at cluster data of each of the at least one lesion cluster comprises a lesion cluster shape complexity or a lesion cluster area, categorizing each of the at least one lesion cluster according to a shape complexity or area of the lesion cluster;
- in a case where a lesion area or a lesion volume for each of the plurality of lesion locations in the medical image is acquired and the lesion cluster data of each of the at least one lesion cluster comprises a mean or median lesion area or a mean or median lesion volume of lesions in the lesion cluster, categorizing each of the at least one lesion cluster according to the mean or median lesion area or the mean or median lesion volume of lesions in the lesion cluster;
- in a case where a lesion shape complexity for each of the plurality of lesion locations in the medical image is acquired and the lesion cluster data of each of the at least one lesion cluster comprises a mean or median lesion shape complexity of lesions in the lesion cluster, categorizing each of the at least one lesion cluster according to the mean or median lesion shape complexity of lesions in the lesion cluster; and
- in a case where a lesion colour or a lesion intensity for each of the plurality of lesion locations in the medical image is acquired and the lesion cluster data of each of the at least one lesion cluster comprises a mean or median lesion colour or a mean or median lesion intensity of lesions in the lesion cluster, categorizing each of the at least one lesion cluster according to mean or median lesion colour or the mean or median lesion intensity of lesions in the lesion cluster.

10. The non-transitory computer-readable storage medium of claim 1, wherein the at least one function comprises at least one of:
- a count function;
- a sum function;
- a mean function;
- a standard deviation function;
- a maximum function; or
- a minimum function.

11. The non-transitory computer-readable storage medium of claim 1, wherein the determined pathologic condition is indicative of any one or more of:
- a presence or absence of a disease in the portion of the subject imaged;
- a severity of a disease in the portion of the subject imaged; and
- a rate of advance of a disease in the portion of the subject imaged.

12. The non-transitory computer-readable storage medium of claim 1, wherein the medical image is any one of:
- an ocular image captured using an ocular imaging system;
- an image of lungs captured using an x-ray imaging system, a computed tomography imaging system, or a low dose computed tomography imaging system;
- an image of a brain captured using a magnetic resonance imaging system; and
- an image of skin captured using a camera.

13. The non-transitory computer-readable storage medium of claim 1, wherein acquiring a location of at least one lesion in the medical image comprises:
- receiving medical image data of the medical image; and
- processing the medical image data in order to determine the location of each of a plurality of lesions in the medical image.

14. An apparatus for determining a pathologic condition that presents as lesions on a portion of a subject from a medical image of the portion of the subject in which the lesions are visible, captured using a medical imaging system, the apparatus comprising:
- an acquiring module configured to acquire a plurality of lesion locations in the medical image from an automated lesion detector that identified the plurality of lesion locations in the medical image;
- a categorizing module configured to:
  - apply a clustering algorithm to the plurality of lesion locations to identify at least one lesion cluster and corresponding lesion cluster data;
  - categorize each lesion cluster of the at least one lesion cluster into at least one category of a set of predetermined categories based on the corresponding lesion cluster data, thereby generating a set of categories from the set of predetermined categories that each comprises one or more lesion clusters of the at least one lesion cluster; and
  - apply, for each category of the generated set of categories, at least one function to the corresponding lesion cluster data for the one or more lesion clusters of the category to generate a predetermined quantity of data outputs for the category, wherein at least one function is a statistical function that takes a set of real numbers and returns a real number; and
- a determining module configured to determine a pathologic condition from the image by using a classification algorithm to process the predetermined quantity of data outputs of each category of the set of categories, wherein the classification algorithm processes a number of inputs that corresponds to the predetermined quantity of data outputs and is trained based on image data defining medical images of the portion of a plurality of subjects using one or more machine learning algorithms.

15. The apparatus of claim 14, wherein the acquiring module is further configured to acquire, as a lesion property, at least one of a type of lesion, a lesion area, a lesion volume, lesion shape complexity, a lesion intensity, and a lesion colour for each of the plurality of lesion locations in the medical image.

16. The apparatus of claim 15, wherein the categorizing module is further configured to apply the clustering algorithm with regard to the plurality of lesion locations having a same lesion property.

17. The apparatus of claim 14, wherein each location of the plurality of lesion locations is defined in a two-dimensional image-based coordinate system or in a coordinate system adapted to the portion of the subject being imaged.

18. The apparatus of claim 14, wherein the clustering algorithm does not require, as input, an indication of a quantity of clusters.

19. The apparatus of claim 14, wherein the clustering algorithm comprises at least one of:
- a density-based spatial clustering of applications with noise, DBSCAN, algorithm; or
- applying a threshold to a bandpass filtered map of the plurality of lesion locations.

20. The apparatus of claim 14, wherein the lesion cluster data include at least one cluster property of each of the at least one lesion cluster, the at least one cluster property comprising one or more of:

in a case where a type of lesion for each of the plurality of lesion locations in the medical image is acquired, a mode type of lesions in the lesion cluster;

in a case where a lesion area or a lesion volume for each of the plurality of lesion locations in the medical image is acquired, a mean or median lesion area or a mean or median lesion volume of lesions in the lesion cluster;

in a case where a lesion shape complexity for each of the plurality of lesion locations in the medical image is acquired, a mean or median lesion shape complexity of lesions in the lesion cluster;

in a case where a lesion intensity or a lesion colour for each of the plurality of lesion locations in the medical image is acquired, a mean or median lesion intensity or a mean or median lesion colour of lesions in the lesion cluster;

a mean location of lesions of the lesion cluster;

a median location of the lesions of the lesion cluster;

a standard deviation of locations of lesions of the lesion cluster;

a variance of locations of lesions of the lesion cluster;

a covariance value of the lesion cluster;

a skewness value of the lesion cluster;

a co-skewness value of the lesion cluster;

a kurtosis value of the lesion cluster;

a co-kurtosis value of the lesion cluster;

a lesion cluster shape complexity; and a lesion cluster area.

* * * * *